(12) United States Patent
Pak et al.

(10) Patent No.: US 6,444,850 B1
(45) Date of Patent: Sep. 3, 2002

(54) FUNGICIDIAL COMPOUNDS HAVING A FLUOROVINYLOXPHYENYL MOIETY AND PROCESS FOR THE PREPARATION THEREOF

(75) Inventors: Chwang-Siek Pak; Bum-Tae Kim; No-Kyun Park; Gyung-Ja Choi; Heung-Tae Kim, all of Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 09/499,937

(22) Filed: Feb. 8, 2000

Related U.S. Application Data

(63) Continuation of application No. PCT/KR98/00245, filed on Aug. 8, 1998.

(30) Foreign Application Priority Data

Aug. 9, 1997 (KR) .............................. 97-38087

(51) Int. Cl.[7] ........................ C07C 233/04; A01N 37/18
(52) U.S. Cl. ...................... 564/164; 514/464; 514/532; 514/534; 514/617; 514/620; 549/442; 560/15; 560/16; 560/56; 560/60; 560/61; 564/182
(58) Field of Search ................................ 514/464, 532, 514/534, 617, 620; 549/442; 560/15, 16, 56, 60, 61; 564/164, 182

(56) References Cited

FOREIGN PATENT DOCUMENTS

JP    56123956    *   9/1981

* cited by examiner

*Primary Examiner*—Shailendra Kumar
(74) *Attorney, Agent, or Firm*—Rosenman & Colin LLP

(57) ABSTRACT

A fungicidal compound of formula (I) having a fluorovinyloxyphenyl moiety and stereoisomers thereof are useful for protecting crops from fungal diseases:

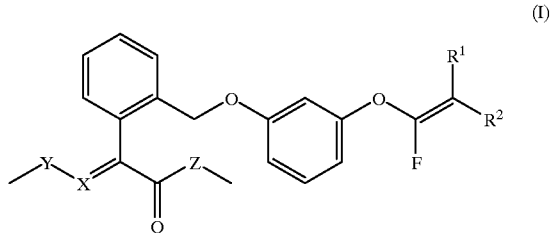

(I)

wherein:

X is CH or N;

Y is O or S;

Z is O or NH;

$R^1$ is hydrogen or $CF_3$; and $R^2$ is hydrogen, a $C_{1-10}$ alkyl, naphthyl, thiophenyl or a phenyl group optionally carrying one or more substituents selected from the group consisting of $C_{1-6}$ alkyl, halogen-substituted $C_{1-6}$ alkyl, $C_{1-6}$ alkoxy, phenoxy, halogen, and methylenedioxy radicals.

5 Claims, No Drawings

FUNGICIDIAL COMPOUNDS HAVING A FLUOROVINYLOXPHYENYL MOIETY AND PROCESS FOR THE PREPARATION THEREOF

This application is a continuation of international application number PCT KR/98/00245, filed Aug. 8, 1998 (status, abandoned, pending, etc.).

FIELD OF THE INVENTION

The present invention relates to novel fungicidal compounds having a fluorovinyloxyphenyl moiety, a process for preparing same and a fungicidal composition containing same as an active ingredient.

DESCRIPTION OF THE PRIOR ART

A number of fungicidal compounds have been in practical use to protect crops from various pathogenic fungi; and they may be classified into several groups having similar structural features. However, the repetitive use of a fungicide over a long period induces the appearance of new fungal strains resistant not only to the particular fungicide but also to related fungicides having common structural features. For this reason, continuous efforts have been undertaken to develop fungicides having new structures.

Such efforts have led to the development of new fungicides, e.g., propenoic ester derived from strobilurin (U.S. Pat. No. 4,994,495; WO 94/19331; and U.S. Pat. No. 5,003,101). However, these propenoic ester derivatives have the problem of limited fungicidal activity.

SUMMARY OF THE INVENTION

Accordingly, it is a primary object of the present invention to provide a novel compound having a superior fungicidal activity against a wide spectrum of plant pathogenic fungi.

It is another object of the present invention to provide a process for the preparation of said compound.

It is a further object of the present invention to provide a fungicidal composition containing said compound.

In accordance with one aspect of the present invention, there are provided a novel compound of formula (I) and stereoisomers thereof:

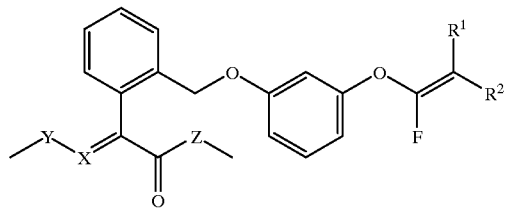

(I)

wherein:
X is CH or N; Y is O or S;
Z is O or NH;
$R^1$ is hydrogen or $CF_3$; and
$R^2$ is hydrogen, a $C_{1-10}$ alkyl, naphthyl, thiophenyl or phenyl group optionally carrying one or more substituents selected from the group consisting of $C_{1-6}$ alkyl, halogen-substituted $c_{1-6}$ alkyl, $C_{1-6}$ alkoxy, phenoxy, halogen and methylenedioxy radicals.

DETAILED DESCRIPTION OF THE INVENTION

The structure of the compound of formula (I) of the present invention is characterized by the fluorovinyloxyphenoxy moiety, but depending on whether X is CH or N, it may also be classified as a propenoic acid derivative (X=CH) or as an iminophenylacetic acid derivative (X=N).

The compound of the present invention has four stereoisomers resulting from two unsymmetrically substituted double bonds, and according to the terminology defined in the Cahn-Ingold-Prelog system (J. March, *Advanced Organic Chemistry*, 3rd Ed., Wiley-Interscience), these four stereoisomers may be expressed as (E,E), (E,Z), (Z,E) and (Z,Z) isomers, which are included within the scope of the present invention.

Among the compounds of the present invention, preferred are those wherein Y is O; Z is O; $R^1$ is hydrogen; and $R^2$ is a naphthyl or phenyl group optionally substituted with methyl, methoxy or halogen; and those wherein Y is O; $R^1$ is $CF_3$; and $R^2$ is a phenyl group optionally substituted with methyl, methoxy or halogen.

The compound of the present invention may be prepared by the steps of (a) reacting a compound of formula (II) with 3-hydroxyphenol (Resorcinol) in the presence of a base to obtain a compound of formula (III); and (b) reacting the compound of formula (III) with a compound of formula (IV) in the presence of a base, as shown in Reaction Scheme A:

Reaction Scheme A

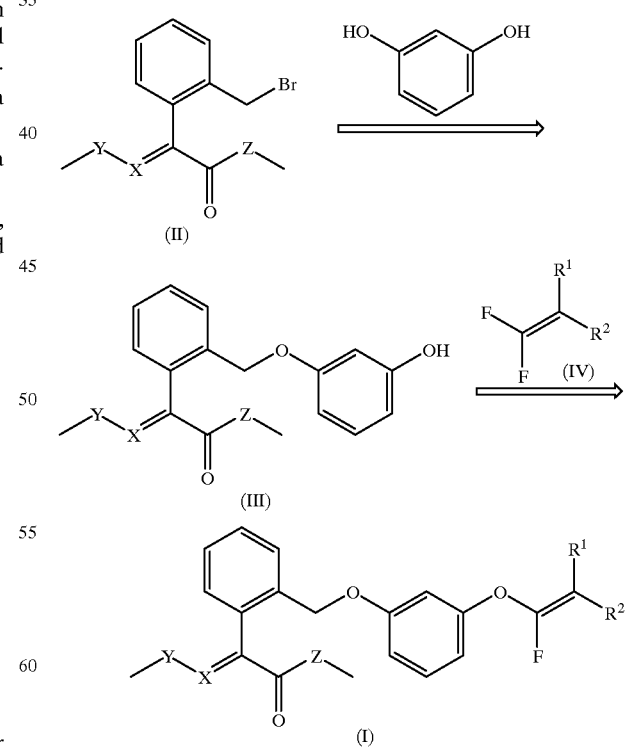

wherein, X, Y, Z, $R^1$ and $R^2$ have the same meanings as defined in formula (I) above.

Representative compounds of formula (II) are those of formula (II-a) (X=CH, Y=O and Z=O), formula (II-b) (X=N, Y=O, Z=O) and formula (II-c) (X=CH, Y=S, Z=O):

(II-a)

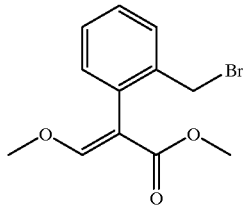

(II-b)

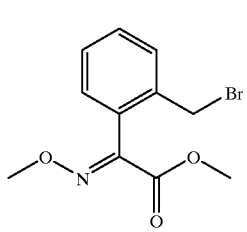

(II-c)

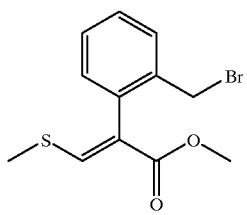

A compound of formula (II-a) may be prepared by esterification, formylation, methylation and bromination of o-tolylacetic acid according to a conventional method (Yamada, K. et al., *Tetrahedron Lett.*, 2745(1973); Vyas, G. N. et al., *Org. Syn. Coll.*, 4, 836(1963); and Kalir, A., *Org. Syn. Coll.*, 5, 825(1973)), as shown in Reaction Scheme B:

Reaction Scheme B

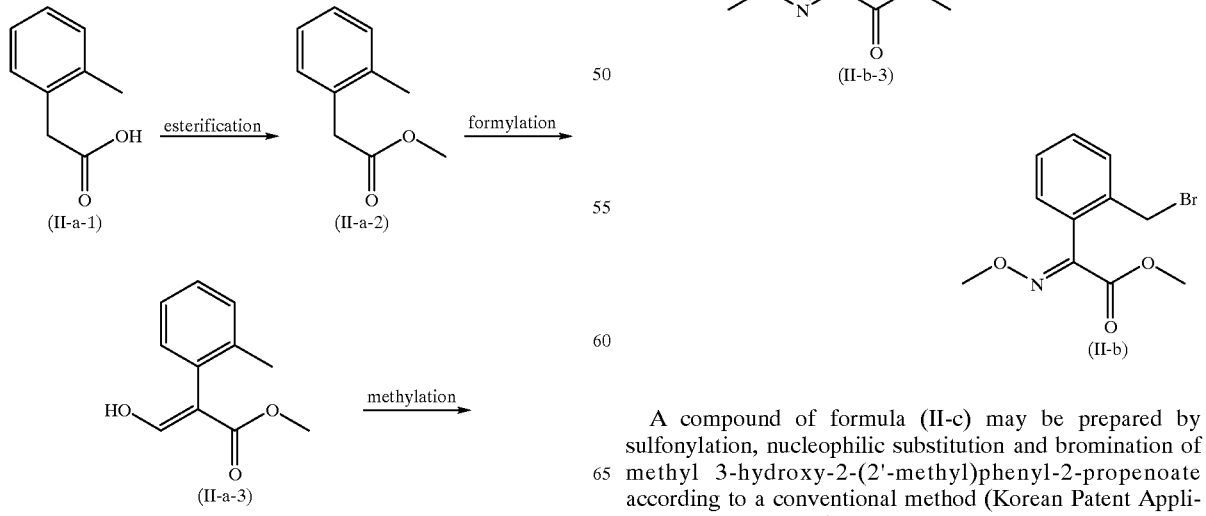

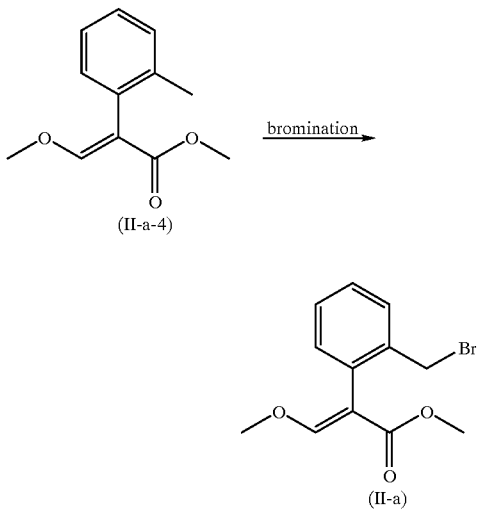

A compound of formula (II-b) may be prepared by Grignard reaction, oxalylation, condensation and bromination of o-bromotoluene according to a conventional method (Rambaud, M. et al., *Synthesis*, 564(1988); Korean Patent No. 88,673; and PCT/KR 95/00020), as shown in Reaction Scheme C:

Reaction Scheme C

A compound of formula (II-c) may be prepared by sulfonylation, nucleophilic substitution and bromination of methyl 3-hydroxy-2-(2'-methyl)phenyl-2-propenoate according to a conventional method (Korean Patent Application No. 95-37559), as shown in Reaction Scheme D:

Reaction Scheme D

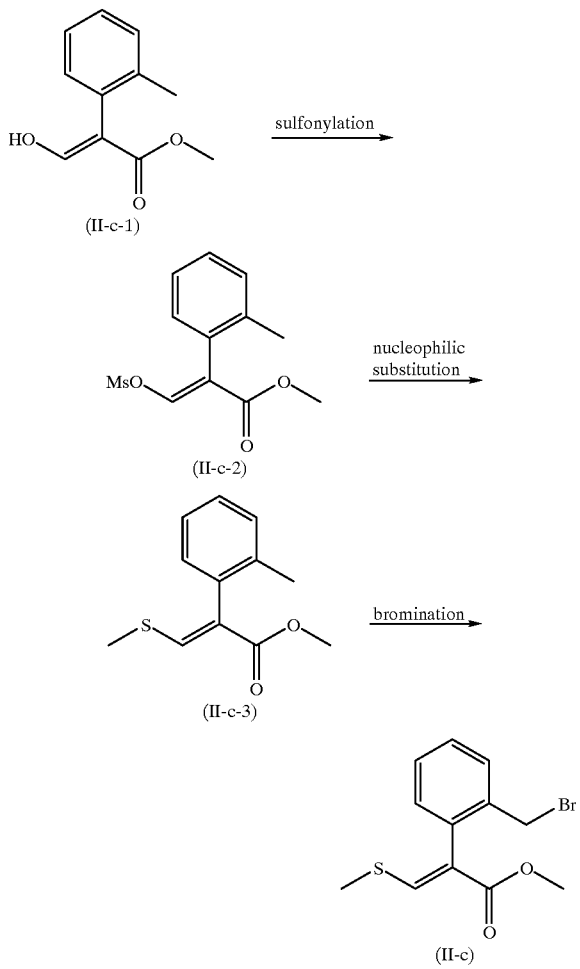

wherein, MsO represents a methansulfonyloxy group.

Representative compounds of formula (III) are those of formula (III-a) (X=CH, Y=O and Z=O), formula (III-b) (X=N, Y=O, Z=O) and formula (III-c) (X=CH, Y=S, Z=O):

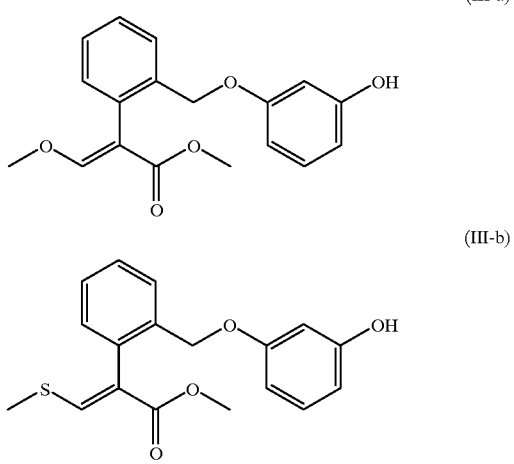

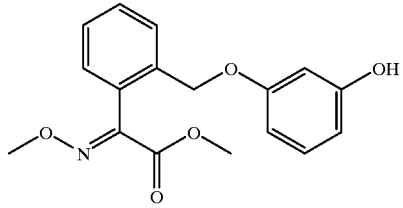

A compound of formula (II) is reacted with 3-hydroxyphenol in the presence of a base to produce a compound of formula (III). The compound of formula (II) and 3-hydroxyphenol may be used in equimolar amounts and the base may be used in twice the molar amount. The base may be an inorganic base, e.g., sodium hydride, potassium t-butoxide, sodium carbonate or potassium carbonate; or an organic base, e.g., triethylamine or pyridine. The solvent which may be used in the reaction includes acetone, benzene, toluene, tetrahydrofuran, acetonitrile, dichloromethane or dimethylformamide, and the reaction may be conducted at a temperature ranging from room temperature to 100° C. The progress of the reaction is conveniently followed by measuring the disappearance of the compound of formula (II) with thin layer chromatography(TLC).

A compound of formula (IV) is reacted with a compound of formula (III) to produce a compound of formula (I), as in Reaction scheme A.

A compound of formula (IV-a), i.e. a compound of formula (IV) wherein $R^1$ is hydrogen, may be prepared by a Grignard reaction, reduction, halogenation, dehalogenation of a halide of $R^2$ according to a conventional method (Herkes, F. E. et al., *J. Org. Chem.*, 32, 1311(1967); and Nemeth, G. et al., *J. fluorine Chem.*, 76, 91(1996)), as shown in Reaction Scheme E:

Reaction Scheme E

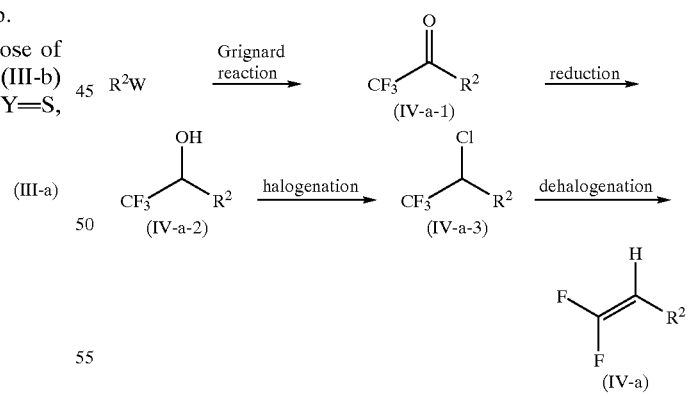

wherein $R^2$ has the same meaning as defined in formula (I) above; and W represents a halogen.

A compound of formula (IV-b), i.e. a compound of formula (IV) wherein $R^1$ is $CF_3$, may be prepared by a Grignard reaction and Wittig reaction of a halide of $R^2$ according to a conventional method (Herkes, F. E. et al., *J. Org. Chem.*, 32, 1311(1967); and Wheatman. G. A. et al., *J. Org. Chem.*, 48, 917(1983)), as shown in Reaction Scheme F:

Reaction Scheme F

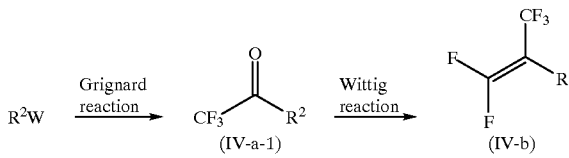

wherein $R^2$ and W have the same meanings as above.

The compound of the present invention may be prepared by reacting a compound of formula (III) with a compound of formula (IV) in the presence of a base. The compounds (III) and (IV) may be used in equimolar amounts and the base may be used in one to two equivalent amounts. The base may be an inorganic base, e.g., sodium hydride, potassium t-butoxide, sodium carbonate or potassium carbonate; or an organic base, e.g., triethylamine or pyridine. The solvent which may be used in the reaction is benzene, toluene, tetrahydrofuran, acetonitrile, dichloromethane or dimethylformamide, and the reaction temperature is in the range of room temperature to 100° C.

In case a mixture of E and Z isomers of compound of formula (II-a-4), (II-b-3) or (II-c-3) is used in the reaction (Reaction Scheme A), the compound of the present invention is obtained as a mixture of four isomers wherein the (E,E) and (E,Z) isomers predominate with minor amounts of the (Z,E) and (Z,Z) isomers. The structures of the four stereoisomers of the compound of the present invention are illustrated below:

In case $R^1$ is hydrogen (E,E) isomer (I-a)

(E,Z) isomer (I-b)

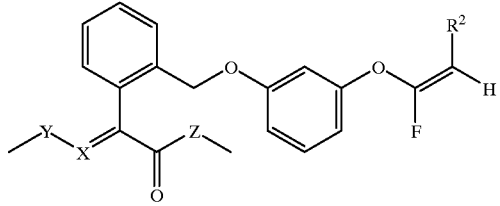

(Z,E) isomer (I-c)

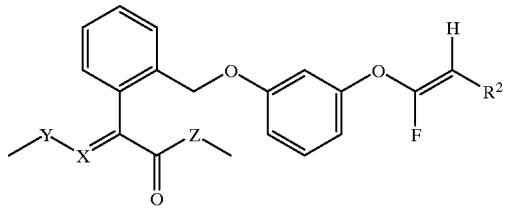

(Z,Z) isomer (I-d)

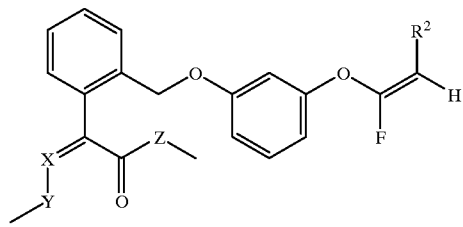

In case $R^1$ is $CF_3$ (E,E) isomer (I-e)

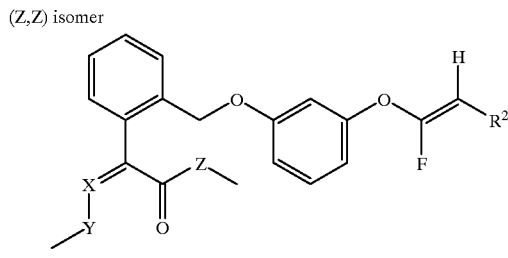

(E,Z) isomer (I-f)

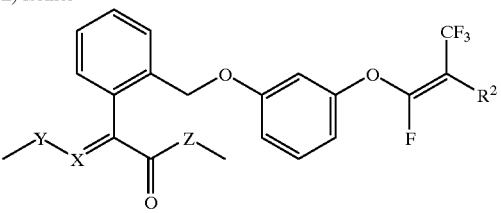

(Z,E) isomer (I-g)

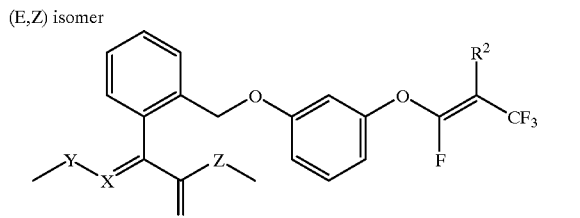

(Z,Z) isomer (I-h)

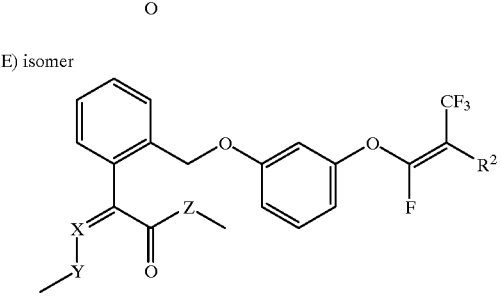

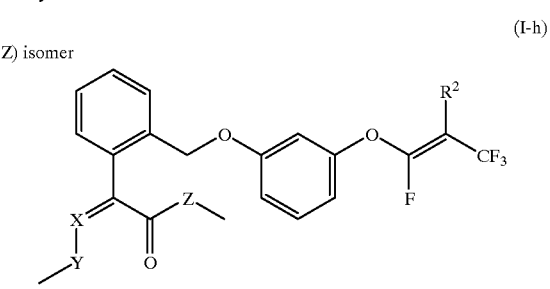

wherein, X, Y, Z, $R^1$ and $R^2$ have the same meanings as defined in formula (I) above.

In case only the E isomer of the compound of formula (II-a-4), (II-b-3) or (II-c-3) is used, the compound of the present invention is obtained as a mixture of the (E,E) and (E,Z) isomers, as is confirmed by $^1$H-NMR or $^{19}$F-NMR analysis.

According to the $^1$H-NMR analysis(reference compound, TMS) of the compound of the present invention wherein $R^1$ is hydrogen, a hydrogen of vinyl group of (E,E) isomer is shown as a doublet having a coupling constant of 5 to 6 Hz at 5.5 to 5.8 ppm, while that of (E,Z) isomer is represented as a doublet having a coupling constant of 30 Hz at 5.0 to 5.4 ppm. The ratio of the (E,E) isomer to (E,Z) isomer is about 3.5:1 which may be calculated from integration on the $^1$H-NMR spectroscopy.

According to the $^{19}$F-NMR analysis data of the compound of the present invention wherein $R^1$ is $CF_3$, a fluorine substituent of vinyl group and fluorine of $CF_3$ of (E,Z) isomer are shown as a quartet having a coupling constant of 23.4 Hz at −75.9 ppm and a doublet having a coupling constant of 23.7 Hz at −58.5 ppm, respectively, while those of (E,E) isomer are represented as a quartet having a coupling constant of 12.6 Hz at −75.3 ppm and a doublet having a coupling constant of 12.6 Hz at −58.7 ppm. The ratio of the (E,Z) isomer to (E,E) isomer is about 2:1 which may be calculated from integration on the $^{19}$F-NMR spectroscopy.

The compound of the present invention wherein Z is NH(the propenamide derivative or iminophenylacetamide derivative of the present invention) may be prepared by reacting the corresponding propenoic ester derivative or iminophenylacetic acid derivative of the present invention with an excess amount of methylamine in an organic solvent, e.g., alcohol including methanol, acetonitrile, dichloromethane or dimethylformamide.

The compound of the present invention has a broad spectrum of fungicidal activity against various plant pathogenic fungus, e.g. *Pyricularia orvzae* Carvara KA301 which causes Rice Blast, *Rhizoctonia solani* AG-1 which causes Rice Sheath Blight, *Botrvtis cinerae* which causes Cucumber Gray Mold Rot, *Phytophthora infestans* which causes Tomato Late Blight, *Puccinia recondita* which causes Wheat Leaf Rust and *Erysiphe graminis* which causes Barley Powdery Mildew.

Accordingly, the present invention also includes within its scope fungicidal compositions comprising one or more of the compounds of formula (I) or stereoisomer thereof as an the compounds of formula (I) or stereoisomer thereof as an active ingredient, in association with fungicidally acceptable carriers.

The fungicidal compositions of the invention may be formulated in various forms such as an emulsion, aqueous dispersion, powder and granules which may contain conventional additives. The compound of the formula (I) may be used in an amount of 10 to 90% on the basis of the weight of an emulsion or aqueous dispersion, and 0.1 to 10% on the basis of the weight of granules.

Fungicidally acceptable carrier that may be used in the present invention is a liquid carrier, e.g., water, an alcohol (ethanol, ethylene glycol, glycerine), ketone (acetone, methylethylketone), ether(dioxane, tetrahydrofuran, cellosolve), aliphatic hydrocarbon (gasoline, Kerosene), halogenated hydrocarbon (chloroform, carbon tetrachloride), amide (dimethylformamide), ester (ethyl acetate, butyl acetate, fatty glycerine ester) and acetonitrile; and a solid carrier, e.g., mineral particle (Kaoline, clay, bentonite, dolomite, talc, silica, sand) and vegetable powder (shrubs).

The additive that may be used in the fungicidal composition of the present invention includes an emulsifier, adhesive, dispersion agent or permeating agent, e.g., nonionic, anionic or cationic interface active agent (fatty acid sodium salt, polyoxy alkyl ester, alkyl sulfonate ester). Further, an agrochemically active ingredient, e.g., an insecticide, herbicide, plant growth regulator, germicide, and fertilizer, may be added in the composition of the present invention.

The following Preparation and Examples are given for the purpose of illustration only and are not intended to limit the scope of the invention.

Preparation 1

Preparation of methyl (2E)-3-methoxy-2-(2'-bromomethyl)phenyl-2-propenoate

Step 1: Preparation of Methyl o-tolylacetate 30.0 g of o-tolylacetic acid (0.2 mol) was dissolved in 100 ml of methanol, 5 ml of concentrated sulfuric acid was added thereto and the resulting solution was stirred with heating for 6 to 12 hours. The resulting solution was cooled and the solvent was removed under a reduced pressure to obtain a residue. The residue was washed twice with water and extracted with ethyl acetate. The organic layer was dried over magnesium sulfate and the solvent was removed under a reduced pressure. The residue thus obtained was subjected to column chromatography using a mixture of n-hexane and ethyl acetate (4:1) as an eluent to obtain 32.15 g (yield 98%) of the title compound as a colorless liquid.

$^1$H-NMR (CDCl$_3$, TMS) δ: 7.21–7.01(m, 4H), 3.61(s, 3H), 3.60(s, 2H), 2.35(s, 3H); MS (m/e): 164(M$^+$, 42), 133(100), 31(82).

Step 2: Preparation of methyl 3-hydroxy-2-(2'-methyl)phenyl-2-propenoate 24.6 g of the compound (0.15 mol) obtained in Step 1 and 24.3 g of sodium methoxide (0.45 mol) were added to 300 ml of toluene, and 27 g of methyl formate (0.45 mol) was added dropwise thereto over a period of 1 hour while cooling and stirring. The resulting solution was stirred at room temperature for 12 hours and extracted twice or three times with water. The combined aqueous layer was acidified with concentrated hydrochloric acid and then extracted with ethyl acetate. The organic layer was dried over magnesium sulfate and then the solvent was removed under a reduced pressure to obtain a residue. The residue was subjected to column chromatography using a mixture of n-hexane and ethyl acetate (9:1) as an eluent to obtain 27.36 g (yield 95%) of the title compound as a colorless liquid.

$^1$H-NMR (CDCl$_3$, TMS) δ: 11.92(d, 1H), 7.32–7.01(m, 4H), 3.71(s, 3H), 2.21(s, 3H); MS (m/e): 192(M$^+$, 26), 160(52), 132(48), 84(100).

Step 3: Preparation of methyl 3-methoxy-2-(2'-methyl)phenyl-2-propenoate 19.2 g of the compound (0.1 mol) obtained in Step 2, 15.12 g of dimethylsulfate (0.12 mol) and 13.82 g of potassium carbonate (0.1 mol) were added to 200 ml of acetone, and the resulting solution was stirred for 12 hours with heating. The solvent was removed under a reduced pressure and the residue was extracted with ethyl acetate. The organic layer was dried over magnesium sulfate and the solvent was removed under a reduced pressure to obtain a residue. The residue was subjected to column chromatography using a mixture of n-hexane and ethyl acetate (4:1) as an eluent to obtain 17.1 g (yield 83%) of the title compound having two isomers as a colorless liquid.

The title compound thus obtained was composed of 82% E isomer and 18% Z isomer.

E isomer(upper spot)

$^1$H-NMR (CDCl$_3$, TMS) δ: 7.51(s, 1H), 7.35–6.98(m, 4H), 3.79(s, 3H), 3.68(s, 3H), 2.21(s, 3H); MS (m/e): 206(M$^+$, 10), 176(73), 117(100), 77(57).

Z isomer(down spot)

$^1$H-NMR (CDCl$_3$, TMS) δ: 7.34–6.98(m, 4H), 6.50(s, 1H), 3.85(s, 3H), 3.68(s, 3H), 2.21(s, 3H); MS (m/e): 206(M$^+$, 8), 176(100), 117(92), 77(30).

These isomers were separated and the E isomer was used in the following step.

Step 4: Preparation of methyl (2E)-3-methoxy-2-(2'-bromomethyl)phenyl-2-propenoate 18.54 gof methyl (2E)-3-methoxy-2-(2'-methyl)phenyl-2-propenoate (0.09 mol) obtained in Step 3 and 16.0 g of N-bromosuccinimide (0.09 mol) were added to 100 ml of carbon tetrachloride. Then, 0.16 g of 2,2'-azobisisobutyronitrile (1 mnol) was added thereto, and the resulting solution was stirred for 12 hours with heating. The resultant solution was cooled and filtered to remove succinimide. The solvent was removed under a reduced pressure and a oily residue thus obtained was subjected to column chromatography using a mixture of n-hexane and ethyl acetate (4:1) as an eluent to obtain 21.73 g (yield 85%) of the title compound as a colorless solid.

Melting Point: 64–65° C. $^1$H-NMR (CDCl$_3$, TMS) δ: 7.63(s, 1H), 7.51–7.09(m, 4H), 4.40(s, 2H), 3.82(s, 3H), 3.69(s, 3H); MS (m/e): 284(M$^+$, 10), 253(12), 205(21), 173(38), 145(100).

Preparation 2

Preparation of methyl (2E)-2-methoxyimino-2-(2'-bromomethyl)phenylacetate

Step 1: Preparation of methyl o-methylbenzoylformate 5.1 g of magnesium (0.21 mol) was placed in 300 ml of dry ether and 34.18 g of o-bromotoluene (0.2 mol) was added dropwise thereto under a nitrogen atmosphere to prepare a Grignard reagent. The Grignard reagent solution was cooled to −78° C. and 23.6 g of dimethyl oxalate (0.2 mol) was added dropwise thereto. The resulting solution was stirred for 30 minutes, mixed with crushed ice, acidified with 20% hydrochloric acid and then extracted with ether. The organic layer was washed three times with water, dried over magnesium sulfate, and the solvent was removed under a reduced pressure to obtain a residue. The residue was subjected to column chromatography using a mixture of n-hexane and ethyl acetate (9:1) as an eluent to obtain 24.2 g (yield 68%) of the title compound as a colorless liquid.

$^1$H-NMR (CDCl$_3$, TMS) δ: 7.88–7.01(m, 4H), 3.98(s, 3H), .65(s, 3H); MS (m/e): 178(M$^+$, 21), 119(100), 91(71), 65(37).

Step 2: Preparation of methyl 2-methoxyimino-2-(2'-ethyl)phenylacetate 8.35 g of O-methylhydroxylamine hydrochloride (0.1 mol) and 8.1 ml of pyridine (0.1 mol) were added to 100 ml of methanol, and then, 17.8 g of the compound (0.1 mol) obtained in Step 1 was added thereto. The resulting solution was stirred for 12 hours with heating and concentrated under a reduced pressure. The resultant solution was mixed with water and extracted with ethyl acetate. The organic layer was dried over magnesium sulfate and the solvent was removed under a reduced pressure to obtain a residue. The residue was subjected to column chromatography using a mixture of n-hexane and ethyl acetate (4:1) as an eluent to obtain 19.04 g (yield 92%) of the title compound as a colorless liquid.

The title compound thus obtained was composed of 50% Z isomer and 50% E isomer. The Z isomer was a liquid and the E isomer was a solid obtained by recrystallization in n-hexane. The structure of E isomer was identified by X-ray crystallography.

Z isomer(upper spot)
$^1$H-NMR (CDCl$_3$, TMS) δ: 7.41–7.15(m, 4H), 4.01(s, 3H), 3.85(s, 3H), 2 45(s, 3H); MS (m/e): 207(M$^+$, 8), 176(41), 116(100), 89(62)

E isomer(down spot)
m.p.: 63–64° C. $^1$H-NMR (CDCl$_3$, TMS) δ: 7.38–7.05(m, 4H), 4.04(s, 3H), 3.85(s, 3H), 2.19(s, 3H); MS (m/e): 207(M$^+$, 11), 176(82), 116(100), 89(70).

The E isomer was employed in following step.

Step 3: Preparation of methyl (2E)-2-methoxyimino-2-(2'-bromomethyl)phenylacetate 9.0 g of methyl (2E)-2-methoxyimino-2-(2'-methyl)phenylacetate (0.0435 mol) obtained in Step 2 and 7.74 g of N-bromosuccinimide (0.0435 mol) were added to 50 ml of carbon tetrachloride, and then, 0.16 g of 2,2'-azobisisobutyronitrile (1 mmol) was added thereto. The resulting solution was stirred for 12 hours with heating, solvent was removed under a reduced pressure and obtained a oily residue which was subjected to silica gel column chromatography using a mixture of n-hexane and ethyl acetate (4:1) as an eluent to obtain 11.08 g (yield 90%) of the title compound as a colorless liquid.

$^1$H-NMR (CDCl$_3$, TMS) δ: 7.62–7.01(m, 4H), 4.39(s, 2H), 4.04(s, 3H),. 3.85(s, 3H); MS (m/e): 285(M$^+$, 46), 252(35), 175(100), 146(94), 116(78).

Preparation 3

Preparation of methyl (2E)-3-thiomethoxy-2-(2'-bromomethyl)phenyl-2-propenoate

Step 1: Preparation of methyl 3-methansulfonyloxy-2-(2'-methyl)phenyl-2-propenoate 17 g of the compound (0.089 mol) obtained in Step 2 of Preparation 1 was dissolved in 400 ml of dry ethyl acetate, and then, 14 ml of triethylamine (0.1 mol) was added thereto under a nitrogen atmosphere. To the resulting solution, 7.74 ml of methansulfonyl chloride (0.1 mol) was added dropwise over a period of 30 minutes with stirring at room temperature. The resultant solution was stirred for 1 to 3 hours, washed three times with water, and then dried over magnesium sulfate. The solvent was removed under a reduced pressure and the residue was subjected to silica gel column chromatography using a mixture of n-hexane and ethyl acetate (4:1) as an eluent to obtain 21.34 g (yield 88.8%) of the title compound as a colorless liquid.

$^1$H-NMR (CDCl$_3$, TMS) δ: 8.01(s, 1H), 7.49–7.01(m, 4H), 3.81(s, 3H), 3.09(s, 3H), 2.23(s, 3H); MS (m/e): 270(M$^+$, 51), 174(100), 159(96), 103(89).

Step 2: Preparation of methyl 3-thiomethoxy-2-(2'-methyl)phenyl-2-propenoate 16.2 g of the compound (0.06 mol) obtained in Step 1 was dissolved in 150 ml of methanol, and then, 4.9 g of sodium thiomethoxide (0.07 mol) was added thereto. The resulting solution was stirred at room temperature for 4 hours, concentrated under a reduced pressure, mixed with water, and then, extracted with ethyl acetate. The organic layer was dried over magnesium sulfate and the solvent was removed under a reduced pressure. The residue was subjected to silica gel column chromatography using a mixture of n-hexane and ethyl acetate (9:1) as an eluent to obtain 10.3 g (yield 77.3%) of the title compound as a colorless liquid.

The title compound thus obtained was composed of 92% E isomer and 8% Z isomer.

E isomer(upper spot)
$^1$H-NMR (CDCl$_3$, TMS) δ: 7.85(s, 1H), 7.38–6.91(m, 4H), 3.75(s, 3H), 2.35(s, 3H), 2.16(s, 3H); MS (m/e): 222(M$^+$, 20), 175(21), 147(36), 115(100).

The E isomer was isolated and employed in the following step.

Step 3: Preparation of methyl (2E)-3-thiomethoxy-2-(2'-bromomethyl)phenyl-2-propenoate 10.2 g of methyl (2E)-3-thiomethoxy-2-(2'-methyl)phenyl-2-propenoate (0.046 mol) obtained in Step 2 and 9.25 g of N-bromosuccinimide (0.052 mol) were added to 150 ml of carbon tetrachloride and 0.16 g- of 2,2'-azobisisobutyronitrile (1 mmol) was added thereto. The resulting solution was stirred for 12 hours with heating, cooled and filtrated to remove succinimide. The solvent was removed under a reduced pressure and the residue was subjected to silica gel column chromatography using a mixture of n-hexane and ethyl acetate (9:1) as an eluent to obtain 8.58 g (yield 62.0%) of the title compound as a colorless liquid.

$^1$H-NMR (CDCl$_3$, TMS) δ: 7.98(s, 1H), 7.69–7.01(m, 4H), 4.45(s, 2H), 3.73(s, 3H), 2.45(s, 3H); MS (m/e): 300(M$^+$, 14), 161(100), 145(30), 115(79).

Preparation 4

Preparation of methyl (2E)-3-methoxy-2-{2'-(3"-hydroxy)phenoxymethyl}phenyl-2-propenoate 5.7 g of compound (0.02 mol) obtained in Preparation 1, 2.2 g of 3-hydroxyphenol (Resorcinol, 0.02 mol) and 2.76 g of potassium carbonate (0.02 mol) were added to 100 ml of acetone and the mixture was ref luxed with heating for 24 hours. The solvent was removed and the resulting mixture was extracted with ethyl acetate. The organic layer was dried over magnesium sulfate and the solvent was removed under a reduced pressure to obtain a residue. The residue was subjected to silica gel column chromatography using a mixture of n-hexane and ethyl acetate (2:1) as an eluent to obtain 4.52 g (yield 72%) of the title compound as a colorless liquid.

$^1$H-NMR (CDCl$_3$, TMS) δ: 7.67(s, 1H), 7.65–6.21(m, 8H), 4.89(s, 2H), 3.78(s, 3H), 3.65(s, 3H), 2.50(br.s, 1H); MS (m/e): 314(M$^+$, 21), 205(98), 174(28), 145(100).

Preparation 5

Preparation of methyl (2E)-2-methoxyimino-2-{2'-(3"-hydroxy)phenoxymethyl}phenylacetate The procedure of Preparation 4 was repeated except that 5.66 g of compound (0.02 mol) obtained in Preparation 2 was used in place of compound obtained in Preparation 1 to obtain 4.92 g (yield 78%) of the title compound as a colorless liquid.

$^1$H-NMR (CDCl$_3$, TMS) δ: 7.54–7.01(m, 9H), 4.89(s, 2H), 4.01(s, 3H), 3.85(s, 3H); MS (m/e): 315(M$^+$, 28), 284(51), 206(86), 132(100), 116(89).

Preparation 6

Preparation of methyl (2E)-3-thiomethoxy-2-{2'-(3"-hydroxy)phenoxymethyl}phenyl-2-propenoate The procedure of Preparation 4 was repeated except that 6.0 g of the compound (0.02 mol) obtained in Preparation 3 was used in place of the compound obtained in Preparation 1 to obtain 3.23 g (yield 49%) of the title compound as a colorless liquid.

$^1$H-NMR (CDCl$_3$, TMS) δ: 7.98(s, 1H), 7.71–6.28(m, 8H), 5.81(br.s, 1H), 4.89(s, 2H), 3.78(s, 3H), 2.35(s, 3H); MS (m/e): 330(M$^+$, 51), 221(77), 161(100), 145(22), 115(54).

PreDaration 7

Preparation of 2,2-difluoro-4'-methoxystyrene
Step 1: Preparation of trifluoromethyl-4'-methoxyphenylketone 5.1 g of magnesium (0.21 mol) was placed in 300 ml of dry diethyl ether and 37.4 g of p-bromoanisole (0.2 mol) was added dropwise thereto under a nitrogen atmosphere to prepare a Grignard reagent. The Grignard reagent solution was cooled to −78° C. and 28.3 g of ethyl trifluoroacetate (0.2 mol) was added dropwise thereto. The resulting solution was stirred for 1 hour, mixed with an crushed ice, acidified with 20% hydrochloric acid and then extracted three times with diethyl ether. The organic layer was dried over magnesium sulfate and the solvent was removed under a reduced pressure to obtain a residue. The residue was distilled at 72 to 73° C./20 mmHg to obtain 35.09 g (yield 86%) of the title compound as a colorless liquid.

$^1$H-NMR (CDCl$_3$, TMS) δ: 7.62–6.81(m, 4H), 3.86(s, 3H); MS (m/e): 204(M$^+$, 56), 135(100), 107(86), 92(66), 77(92).

Step 2: Preparation of 1-hydroxy-2,2,2-trifluoroethyl-4'-methoxybenzene 14.28 g of compound (150 ml) obtained in Step 1 was dissolved in 150 ml of methanol and 1.32 g of sodium borohydride (0.035 mol) was added dropwise thereto for 30 minutes. The resulting solution was stirred at room temperature for 2 hours and the solvent was removed. Ethyl acetate was added thereto and the resultant solution was washed three times with water. The organic layer was dried over magnesium sulfate and the solvent was removed under a reduced pressure to obtain a residue. The residue was subjected to silica gel column chromatography using a mixture of n-hexane and ethyl acetate (4:1) as an eluent to obtain 14 g (yield 97%) of the title compound as a colorless liquid.

$^1$H-NMR (CDCl$_3$, TMS) δ: 7.62–6.78(m, 4H), 4.29(q, 1H), 3.94(br.s, 1H), 3.86(s, 3H); MS (m/e): 206(M$^+$, 42), 191(62), 137(100), 107(26), 69(56).

Step 3: Preparation of 1-chloro-2,2,2-trifluoroethyl-4'-methoxybenzene 14 g of the compound (0.068 mol) obtained in Step 2 and 50 g of thionyl chloride (0.7 mol) were added to 100 ml of toluene and the mixture was stirred with heating for 12 hours. The resulting solution was cooled and washed with water. The organic layer was dried over magnesium sulfate and the solvent was removed under a reduced pressure to obtain a residue. The residue was subjected to silica gel column chromatography using n-hexane as an eluent to obtain 12 g (yield 79%) of the title compound as a colorless liquid.

$^1$H-NMR (CDCl$_3$, TMS) δ: 7.62–6.81(m, 4H), 5.01(q, 1H), 3.86(s, 3H); MS (m/e): 224(M$^+$, 23), 189(100), 158(79), 120(56), 69(43).

Step 4: Preparation of 2,2-difluoro-4'-methoxystyrene 11.2 g of the compound (0.05 mol) obtained in Step 3 was dissolved in 50 ml of dry tetrahydrofuran, and then, 3.27 g of activated zinc (0.05 mol) was added thereto. The resulting solution was ref luxed for 12 hours while stirring and heating. The resulting solution was cooled and filtered to remove precipitated salts. The solvent was removed under a reduced pressure and the residue was subjected to silica gel column chromatography using n-hexane as an eluent to obtain 6.8 g (yield 80%) of the title compound as a colorless liquid.

$^1$H-NMR (CDCl$_3$, TMS) δ: 7.51–6.69(m, 4H), 5.29(dd, 1H, J=26 Hz, J=4 Hz), 3.86(s, 3H); MS (m/e): 170(M$^+$, 100), 155(68), 127(92), 84(21).

Preparations 8 to 20

The procedure of Preparation 7 was repeated to obtain intermediate compounds of formulas (IV-a-1), (IV-a-2), (IV-a-3) and (IV-a) having various R$^2$ groups, as in Tables 1a, 1b, 1c and 1d, respectively. The $^1$H-NMR and MS analysis data of these compounds are also shown in respective tables.

TABLE 1a

Compounds of Formula (IV-a-1)

| Prep. No. | $R^2$ | $^1$H—NMR (CDCl$_3$, TMS) δ (ppm) | MS (m/e) | Yield (%) | b.p. (mmHg) |
|---|---|---|---|---|---|
| 8  | C$_6$H$_5$— | 7.52~7.12(m, 5H) | 174(21), 105(100), 77(82), 69(54) | 71 | 64~65 (33) |
| 9  | 2-CH$_3$—C$_6$H$_4$— | 7.78~7.03(m, 4H), 2.38(s, 3H) | 188(41), 170(57), 108(100), 91(83), 45(47) | 54 | 72~73 (40) |
| 10 | 3-CH$_3$—C$_6$H$_4$— | 7.52~6.92(m, 4H), 2.25(s, 3H) | 188(16), 135(45), 119(96), 91(100), 65(45) | 61 | 70~71 (20) |
| 11 | 4-CH$_3$—C$_6$H$_4$— | 7.42~6.92(m, 4H), 2.25(s, 3H) | 188(12), 119(100), 91(96), 65(45) | 68 | 79~80 (22) |
| 12 | 3,4-(CH$_3$)$_2$—C$_6$H$_3$— | 7.52~6.69(m, 3H), 3.86(s, 3H) | 202(43), 133(98), 69(100) | 71 | Column |
| 13 | 3,5-(CH$_3$)$_2$—C$_6$H$_3$— | 7.31~7.01(m, 3H), 2.25(s, 6H) | 202(24), 133(100), 69(24) | 69 | Column |
| 14 | 2,4,5-(CH$_3$)$_3$—C$_6$H$_2$— | 7.48~6.98(m, 2H), 2.32(s, 3H), 2.28(s, 6H) | 216(24), 119(100), 97(23), 69(54) | 72 | 80~81 (6) |
| 15 | 3-CH$_3$O—C$_6$H$_4$— | 7.41~6.79(m, 4H), 3.79(s, 3H) | 204(36), 135(100), 107(56), 77(94) | 78 | 64~65 (33) |
| 16 | 4-C$_6$H$_5$O—C$_6$H$_4$— | 7.59~6.69(m, 9H) | 266(42), 197(100), 104(63), 97(53), 69(52) | 71 | Column |
| 17 | 3-F—C$_6$H$_4$— | 7.56~6.89(m, 4H)) | 192(25), 123(100), 95(78), 75(31) | 54 | 59~60 (30) |
| 18 | 4-F—C$_6$H$_4$— | 7.76~6.92(m, 4H) | 192(16), 169(54), 123(100), 95(91), 75(76) | 59 | 66~67 (34) |
| 19 | 4-Cl—C$_6$H$_4$— | 7.51~7.41(m, 4H) | 208(100), 173(92), 97(54), 69(24) | 61 | 83~84 (24) |
| 20 | C$_{10}$H$_7$— | 7.98~7.32(m, 7H) | 224(25), 155(100), 69(54) | 65 | Column |

TABLE 1b

Compounds of Formula (IV-a-2)

| Prep. No. | $R^2$ | $^1$H—NMR (CDCl$_3$, TMS) δ (ppm) |
|---|---|---|
| 8  | C$_6$H$_5$— | 7.54~7.13(m, 5H), 4.87(q, 1H), 4.29(br.s, 1H) |
| 9  | 2-CH$_3$—C$_6$H$_4$— | 7.78~7.03(m, 4H), 5.19(q, 1H), 2.81(br.s, 1H), 2.38(s, 3H) |
| 10 | 3-CH$_3$—C$_6$H$_4$— | 7.53~7.01(m, 4H), 4.87(q, 1H), 4.29(br.s, 1H), 2.24(s, 3H) |
| 11 | 4-CH$_3$—C$_6$H$_4$— | 7.45~6.92(m, 4H), 4.87(q, 1H), 4.30(br.s, 1H), 2.23(s, 3H) |
| 12 | 3,4-(CH$_3$)$_2$—C$_6$H$_3$— | 7.37~7.09(m, 3H), 4.95(q, 1H), 2.50(br.s, 3H), 2.26(s, 6H) |
| 13 | 3,5-(CH$_3$)$_2$—C$_6$H$_3$— | 7.32~7.01(m, 3H), 4.98(q, 1H), 2.48(br.s, 1H), 2.25(s, 6H) |
| 14 | 2,4,5-(CH$_3$)$_3$—C$_6$H$_2$— | 7.48~6.98(m, 2H), 5.31(q, 1H), 2.48(br.s, 3H), 2.32(s, 3H), 2.28(6H) |
| 15 | 3-CH$_3$O—C$_6$H$_4$— | 7.45~6.79(m, 4H), 4.94(q, 1H), 3.79(s, 3H), 3.21(br.s, 1H) |
| 16 | 4-C$_6$H$_5$O—C$_6$H$_4$— | 7.58~6.89(m, 9H), 4.93(q, 1H), 2.69(br.s, 1H) |
| 17 | 3-F—C$_6$H$_4$— | 7.56~6.87(m, 4H), 4.95(q, 1H), 3.24(br.s, 1H) |
| 18 | 4-F—C$_6$H$_4$— | 7.76~6.92(m, 4H), 4.98(q, 1H), 3.18(br.s, 1H) |
| 19 | 4-Cl—C$_6$H$_4$— | 7.51~7.41(m, 4H), 4.97(q, 1H), 3.61(br.s, 1H) |
| 20 | C$_{10}$H$_7$— | 8.12~7.28(m, 7H), 5.92(q, 1H), 2.54(br.s, 1H) |

| Prep. No. | MS (m/e) | Yield (%) | b.p. (mmHg) |
|---|---|---|---|
| 8  | 176(39), 107(100), 79(91) | 98 | 50~51 (1) |
| 9  | 190(10), 121(36), 84(100) | 87 | Column |
| 10 | 190(24), 121(46), 84(100) | 89 | Column |
| 11 | 190(24), 121(100), 91(96), 69(45) | 89 | Column |
| 12 | 204(21), 187(59), 118(100), 99(32), 69(54) | 88 | Column |
| 13 | 204(42), 187(42), 118(100), 99(24), 69(23) | 84 | Column |
| 14 | 218(52), 201(24), 119(82), 69(100) | 89 | Column |
| 15 | 206(39), 137(53), 109(99), 94(75), 84(100) | 88 | Column |
| 16 | 268(52), 199(59), 169(100), 97(82), 69(53) | 98 | Column |
| 17 | 194(100), 177(82), 124(54), 97(82) | 82 | Column |
| 18 | 194(100), 177(14), 124(47), 97(96) | 81 | 64~64 (33) |
| 19 | 210(52), 141(100), 111(23), 99(49), 69(82) | 76 | Column |
| 20 | 226(54), 127(100), 99(25), 69(45) | 87 | Column |

TABLE 1c

Compounds of Formula (IV-a-3)

| Prep. No. | $R^2$ | $^1$H—NMR (CDCl$_3$, TMS) δ (ppm) | MS (m/e) | Yield (%) | b.p. (mmHg) |
|---|---|---|---|---|---|
| 8  | C$_6$H$_5$— | 7.62~7.15(m, 5H), 5.10(q, 1H) | 194(94), 125(100), 83(30), 44(81) | 72 | Column |
| 9  | 2-CH$_3$—C$_6$H$_4$— | 7.82~7.01(m, 4H), 5.29(q, 1H), 2.38(s, 3H) | 208(42), 173(100), 104(79), 69(45) | 89 | Column |
| 10 | 3-CH$_3$—C$_6$H$_4$— | 7.49~7.01(m, 4H), 5.01(q, 1H), 2.24(s, 3H) | 208(52), 173(100), 104(26), 69(23) | 82 | Column |
| 11 | 4-CH$_3$—C$_6$H$_4$— | 7.42~6.92(m, 4H), 5.01(q, 1H), 2.26(s, 3H) | 208(64), 173(92), 104(100), 69(28) | 65 | Column |
| 12 | 3,4-(CH$_3$)$_2$—C$_6$H$_3$— | 7.38~7.02(m, 3H), 5.01(q, 1H), 2.25(s, 6H) | 222(36), 187(56), 117(100) | 86 | Column |
| 13 | 3,5-(CH$_3$)$_2$—C$_6$H$_3$— | 7.29~7.01(m, 3H), 5.02(q, 1H), 2.25(s, 6H) | 222(32), 187(24), 117(100) | 82 | Column |
| 14 | 2,4,5-(CH$_3$)$_3$—C$_6$H$_2$— | 7.48~6.98(m, 2H), 5.43(q, 1H), 2.32(s, 3H), 2.28(6H) | 236(20), 201(100), 167(39) | 88 | Column |
| 15 | 3-CH$_3$O—C$_6$H$_4$— | 7.51~6.80(m, 4H), 5.10(q, 1H), 3.80(s, 3H) | 224(10), 86(100) | 79 | Column |
| 16 | 4-C$_6$H$_5$O—C$_6$H$_4$— | 7.62~6.88(m, 9H), 5.15(q, 1H) | 286(25), 251(32), 182(100), 117(54), 69(52) | 98 | Column |
| 17 | 3-F—C$_6$H$_4$— | 7.56~6.87(m, 4H), 5.03(q, 1H) | 212(42), 177(100), 60(52) | 76 | Column |
| 18 | 4-F—C$_6$H$_4$— | 7.76~6.91(m, 4H), 5.10(q, 1H) | 212(23), 177(100), 69(39) | 76 | Column |

TABLE 1c-continued

Compounds of Formula (IV-a-3)

| Prep. No. | $R^2$ | $^1$H—NMR (CDCl$_3$, TMS) δ (ppm) | MS (m/e) | Yield (%) | b.p. (mmHg) |
|---|---|---|---|---|---|
| 19 | 4-Cl—C$_6$H$_4$— | 7.51~7.41(m, 4H), 5.02(q, 1H) | 228(100), 111(54), 69(52) | 76 | Column |
| 20 | C$_{10}$H$_7$— | 8.12~7.36(m, 7H), 6.01(q, 1H) | 244(100), 127(69), 117(54) | 86 | Column |

TABLE 1d

Compounds Formula (IV-a)

| Prep. No. | $R^1$ | $R^2$ | $^1$H—NMR (CDCl$_3$, TMS) δ (ppm) |
|---|---|---|---|
| 8 | H | C$_6$H$_5$— | 7.45~7.10(m, 5H), 5.20(d, d, 1H, J=26Hz, J=4Hz) |
| 9 | H | 2-CH$_3$—C$_6$H$_4$— | 7.82~7.01(m, 4H), 5.23(d, d, 1H, J=26Hz, J=4Hz), 2.25(s, 3H) |
| 10 | H | 3-CH$_3$—C$_6$H$_4$— | 7.48~6.92(m, 4H), 5.21(d, d, 1H, J=26Hz, J=4Hz), 2.28(s, 3H) |
| 11 | H | 4-CH$_3$—C$_6$H$_4$— | 7.45~6.89(m, 4H), 5.26(d, d, 1H, J=26Hz, J=4Hz), 2.27(s, 3H) |
| 12 | H | 3,4-(CH$_3$)$_2$—C$_6$H$_3$— | 7.32~7.02(m, 3H), 5.27(d, d, 1H, J=26Hz, J=4Hz), 2.22(s, 6H) |
| 13 | H | 3,5-(CH$_3$)$_2$—C$_6$H$_3$— | 7.01~6.89(m, 3H), 5.20(d, d, 1H, J=26Hz, J=4Hz), 2.24(s, 6H) |
| 14 | H | 2,4,5-(CH$_3$)$_3$—C$_6$H$_2$— | 7.28~6.89(m, 2H), 5.21(d, d, 1H, J=26Hz, J=4Hz), 2.21(s, 9H) |
| 15 | H | 3-CH$_3$O—C$_6$H$_4$— | 7.50~6.69(m, 4H), 5.19(d, d, 1H, J=26Hz, J=4Hz), 3.79(s, 3H) |
| 16 | H | 4-C$_6$H$_5$O—C$_6$H$_4$— | 7.68~6.82(m, 9H), 5.24(d, d, 1H, J=26Hz, J=4Hz) |
| 17 | H | 3-F—C$_6$H$_4$— | 7.59~6.78(m, 4H), 5.21(d, d, 1H, J=26Hz, J=4Hz) |
| 18 | H | 4-F—C$_6$H$_4$— | 7.76~6.91(m, 4H), 5.25(d, d, 1H, J=26Hz, J=4Hz) |
| 19 | H | 4-Cl—C$_6$H$_4$— | 7.48~7.29(m, 4H), 5.23(d, d, 1H, J=26Hz, J=4Hz) |
| 20 | H | C$_{10}$H$_7$— | 8.13~7.45(m, 7H), 5.81(d, d, 1H, J=26Hz, J=4Hz) |

| Prep. No. | MS (m/e) | Yield (%) | b.p. (mmHg) |
|---|---|---|---|
| 8 | 140(100), 120(26), 84(16), 44(32) | 87 | 58~59 (49) |
| 9 | 154(48), 135(54), 65(54), 45(100) | 92 | Column |
| 10 | 154(39), 135(29), 64(41), 45(100) | 87 | Column |
| 11 | 154(100), 135(62), 45(54) | 86 | Column |
| 12 | 168(32), 133(49), 44(100) | 91 | Column |
| 13 | 168(82), 153(46), 84(100), 62(59) | 98 | Column |
| 14 | 182(100), 167(92), 144(73), 84(98), 44(52) | 88 | Column |
| 15 | 170(100), 140(36), 127(42), 77(24) | 98 | 33~34 (1) |
| 16 | 232(100), 213(54), 120(84), 93(42) | 76 | Column |
| 17 | 158(21), 84(100), 47(42) | 75 | Column |
| 18 | 158(100), 39(27) | 88 | Column |
| 19 | 174(58), 139(36), 119(29), 84(100), 49(56) | 81 | Column |
| 20 | 190(89), 170(100), 138(28), 85(44) | 90 | Column |

Preparation 21

Preparation of 2,2-difluoro-1-trifluoromethyl-4'-methoxy styrene 26.2 g of triphenylphosphine (0.1 mol) was dissolved in 250 ml of dry triglyme and 25.2 g of dibromodifluoromethan (0.12 mol) was added dropwise thereto under a nitrogen atmosphere at a temperature below 10° C. To the resulting solution was added 10.2 g of compound (0.05 mol) obtained in Step 1 of Preparation 7. The resultant solution was stirred at 100° C. with heating for 12 hours, cooled and distilled under a reduced pressure. The obtained oil was redistilled to obtain 9.39 g of a title compound having a temperature of 72 to 74° C. at 10 mmHg as a colorless liquid.

$^1$H-NMR (CDCl$_3$, TMS) δ: 7.48–6.79(m, 4H), 3.79(s, 3H); MS (m/e): 238(M$^+$, 69), 195(14), 145(35), 74(33), 59(100).

Preparations 22 to 40

Using each of the compounds of formula (IV-a-1) listed in Table 1a and Table 2a, the procedure of Preparation 21 was repeated to obtain compounds of formula (IV-b) having various $R^2$ groups, as shown in Table 2b. The $^1$H-NMR and MS data of these compounds are also listed in Table 2b.

TABLE 2a

Compounds of Formula (IV-a-1)

| Prep. No. | $R^2$ | $^1$H—NMR (CDCl$_3$, TMS) δ (ppm) | MS (m/e) | Yield (%) | b.p. (mmHg) |
|---|---|---|---|---|---|
| 25 | 4-C$_2$H$_5$—C$_6$H$_4$— | 7.46~7.19(m, 4H), 2.68(q, 2H), 1.23(t, 3H) | 202(40), 133(91), 105(100), 76(64) | 62 | Column |
| 26 | 4-n-C$_4$H$_9$—C$_6$H$_4$— | 8.14~7.29(m, 4H), 2.24(t, 2H), 1.96~1.03(m, 4H), 0.94(t, 3H) | 230(15), 161(100), 118(18), 91(55) | 52 | Column |
| 30 | 4-C$_2$H$_5$O—C$_6$H$_4$— | 7.54~6.76(m, 4H), 4.09(q, 2H), 1.32(t, 3H) | 218(16), 149(88), 121(62), 76(100) | 69 | Column |
| 31 | 3,4-OCH$_2$O—C$_6$H$_4$— | 7.92~7.43(m, 3H), 6.25~6.01(s, 2H) | 218(42), 149(100), 65(49) | 73 | Column |
| 32 | 3-CF$_4$—C$_6$H$_4$— | 8.60~7.61(m, 4H) | 242(10), 173(68), 145(100), 76(62) | 67 | Column |

TABLE 2a-continued

Compounds of Formula (IV-a-1)

| Prep. No. | R² | ¹H—NMR (CDCl₃, TMS) δ (ppm) | MS (m/e) | Yield (%) | b.p. (mmHg) |
|---|---|---|---|---|---|
| 33 | 3-Cl—C₆H₄— | 8.38~7.45(m, 4H) | 208(10), 139(93), 111(100), 75(64) | 70 | 58~59 (10) |
| 37 | 4-Br—C₆H₄— | 7.44~7.16(m, 4H) | 252(31), 184(100), 104(32) | 42 | Column |
| 38 | 3,5-Cl₂—C₆H₄— | 8.12~7.86(m, 3H) | 242(55), 173(100), 145(64), 109(32) | 45 | 75~76 (4) |
| 39 | C₄H₃S-2-yl- | 8.28~7.28(m, 3H) | 180(23), 111(45), 84(100) | 76 | Column |
| 40 | n-C₆H₁₃— | 3.02(t, 2H), 1.98~1.02(m, 8H), 0.98(t, 3H) | 182(25), 114(46), 86(100) | 52 | Column |

TABLE 2b

Compounds of Formula (IV-b)

| Prep. No. | R¹ | R² | ¹H—NMR (CDCl₃, TMS) δ (ppm) |
|---|---|---|---|
| 22 | CF₃ | C₆H₅— | 7.59~7.31(m, 5H) |
| 23 | CF₃ | 3-CH₄—C₆H₄— | 7.46~6.98(m, 4H), 2.43(s, 3H) |
| 24 | CF₃ | 4-CH₄—C₆H₄— | 7.32~7.18(m, 4H), 2.45(s, 3H) |
| 25 | CF₃ | 4-C₂H₅—C₆H₄— | 7.38~7.25(m, 4H), 2.68(q, 2H), 1.19(t, 3H) |
| 26 | CF₃ | 4-n-C₄H₉—C₆H₄— | 7.32~7.25(m, 4H), 2.69(t, 2H), 2.01~1.23(m, 4H), 1.09(t, 3H) |
| 27 | CF₃ | 3,4-(CH₃)₂—C₆H₄— | 7.28~7.02(m, 3H), 2.38(s, 3H), 2.32(s, 3H) |
| 28 | CF₃ | 3,5-(CH₃)₂—C₆H₃— | 7.32~7.12(m, 3H), 2.41(s, 6H) |
| 29 | CF₃ | 3-CH₃O—C₆H₄— | 7.48~6.87(m, 4H), 3.81(s, 3H) |
| 30 | CF₃ | 4-C₂H₅O—C₆H₄— | 7.51~6.85(m, 4H), 4.12(q, 2H), 1.29(t, 3H) |
| 31 | CF₃ | 3,4-OCH₂O—C₆H₄— | 7.01~6.79(m, 3H), 6.01(s, 2H) |
| 32 | CF₃ | 3-CF₄—C₆H₄— | 7.82~7.18(m, 4H) |
| 33 | CF₃ | 3-Cl—C₆H₄— | 7.54~7.23(m, 4H) |
| 34 | CF₃ | 4-Cl—C₆H₄— | 7.56~7.21(m, 4H) |
| 35 | CF₃ | 3-F—C₆H₄— | 7.53~6.96(m, 4H) |
| 36 | CF₃ | 4-F—C₆H₄— | 7.52~6.83(m, 4H) |
| 37 | CF₃ | 4-Br—C₆H₄— | 7.81~7.19(m, 4H) |
| 38 | CF₃ | 3,5-Cl₂—C₆H₄— | 7.57~7.19(m, 3H) |
| 39 | CF₃ | C₄H₅S-2-yl | 7.67~6.92(m, 3H) |
| 40 | CF₃ | n-C₆H₁₄— | 2.45~1.98(t, 2H), 1.71~1.19(m, 8H), 0.98(t, 3H) |

| Prep. No. | MS (m/e) | Yield (%) | b.p. (mmHg) |
|---|---|---|---|
| 22 | 208(48), 84(83), 43(100) | 67 | Column |
| 23 | 222(20), 203(70), 134(100) | 45 | Column |
| 24 | 222(64), 203(23), 134(100) | 62 | Column |
| 25 | 236(20), 145(100), 90(54) | 62 | column |
| 26 | 264(30), 221(37), 151(36), 84(100), 57(50) | 58 | Column |
| 27 | 236(18), 84(33), 45(100) | 78 | Column |
| 28 | 236(29), 217(68), 148(100), 45(92) | 98 | Column |
| 29 | 238(42), 207(45), 188(37), 139(100), 69(94) | 54 | 75 (10) |
| 30 | 252(47), 233(100), 84(64) | 73 | Column |
| 31 | 252(46), 233(63), 164(82), 69(100) | 72 | Column |
| 32 | 276(52), 257(92), 188(100) | 52 | Column |
| 33 | 242(26), 223(72), 188(49), 69(100) | 63 | Column |
| 34 | 242(35), 207(25), 174(70), 139(100), 60(79) | 45 | 58 (10) |
| 35 | 226(52), 207(25), 84(100) | 54 | Column |
| 36 | 226(20), 84(100) | 63 | Column |
| 37 | 286(100), 207(86), 138(66), 69(57) | 43 | Column |
| 38 | 276(100), 241(45) | 84 | 85 (10) |
| 39 | 214(42), 195(92), 126(100), 47(86) | 63 | Column |
| 40 | 216(32), 197(20), 84(100) | 58 | Column |

EXAMPLE 1

Preparation of methyl (2E)-3-methoxy-2-{2'-{3"-(2'"-fluorostyryl)-2'"-oxy}phenoxymethyl}phenyl-2-propenoate (Compound 1)

314 mg of the compound (1 mmol) obtained in Preparation 4 was added to 10 ml of acetonitrile and 40 mg of sodium hydride (1 mol) dispersed in mineral oil (60%) was added thereto under a nitrogen atmosphere. The resulting solution was stirred for 30 minutes and 140 mg of the compound (1 mmol) obtained in Preparation 8 was added slowly thereto. The resultant solution was stirred for 4 hours with heating, mixed with water and extracted with ethyl acetate. The organic layer was dried over magnesium sulfate and the solvent was removed under a reduced pressure. The residue was subjected to silica gel column chromatography using a mixture of n-hexane and ethyl acetate (4:1) as an eluent to obtain 400 mg (yield 92%) of the title compound as a colorless liquid.

¹H-NMR (CDCl₃, TMS) δ: 7.68(s, 1H), 7.62–6.62(m, 13H), 5.68(d, 1H), 4.98(s, 2H), 3.78(s, 3H), 3.69(s, 3H); MS (m/e): 434(M⁺, 13), 205(87), 145(100).

EXAMPLE 2

Preparation of (2E)-N-methyl-3-methoxy-2-{2'-{3"-(2'"-fluorostyryl)-2'"-oxy}phenoxymethyl}phenyl-2-propenamide (Compound 2)

217 mg of the compound 1(0.5 mmol) obtained in Example 1 was dissolved in 5 ml of methanol and 2 ml of aqueous methylamine solution(40%) were added thereto. The resulting solution was stirred for 12 hours and the solvent was removed under a reduced pressure. The resultant solution was extracted with ethyl acetate and the organic layer was dried over magnesium sulfate. The solvent was removed under a reduced pressure and the residue was subjected to silica gel column chromatography using a mixture of n-hexane and ethyl acetate (4:1) as an eluent to obtain 206 mg (yield 95%) of the title compound as a colorless liquid.

$^1$H-NMR (CDCl$_3$, TMS) δ: 8.12(br, 1H), 7.62–6.58(m, 14H), 5.62(d, lH), 4.98(s, 2H), 3.69(s, 3H), 2.78(d, 3H); MS (m/e): 433(M$^+$, 6), 204(41), 144(100), 103(24).

EXAMPLES 3 TO 44

Using each of the compounds obtained in Preparations 4 to 20, the procedure of Example 1 or 2 was repeated to obtain 42 compounds (Compound 3 to 44) of formula (I) of the present invention having various R$^2$ groups listed in Table 3. The $^1$H-NMR and MS data of these compounds are also shown in Table 3.

TABLE 3

Compounds of formula (I)

| Compound No. | X | Y | Z | R$^1$ | R$^2$ | $^1$H—NMR (CDCl$_3$, TMS) δ (ppm) | MS (m/e) |
|---|---|---|---|---|---|---|---|
| 1 | CH | O | O | H | C$_6$H$_5$ | 7.68(s, 1H), 7.62~6.62(m, 13H), 5.68(d, 1H), 4.98(s, 2H), 3.78(s, 3H), 3.69(s, 3H) | 434(13), 205(87), 145(100) |
| 2 | CH | O | NH | H | C$_6$H$_5$ | 8.12(br, 1H), 7.62~6.58(m, 14H), 5.62(d, 1H), 4.98(s, 2H), 3.69(s, 3H), 2.78(d, 3H) | 433(6), 204(41), 144(100), 103(24) |
| 3 | N | O | O | H | C$_6$H$_5$ | 7.78~6.58(m, 13H), 5.62(d, 1H), 4.92(s, 2H), 3.98(s, 3H), 3.79(s, 3H) | 453(3), 260(20), 131(24), 116(100) |
| 4 | CH | S | O | H | C$_6$H$_5$ | 7.92(s, 1H), 7.72~6.62(m, 13H), 5.68(d, 1H), 4.98(s, 2H), 3.69(s, 3H), 2.32(s, 3H) | 450(40), 221(98), 151(100), 115(58) |
| 5 | CH | O | O | H | 2-CH$_3$—C$_6$H$_4$ | 7.68(s, 1H), 7.62~6.58(m, 12H), 5.68(d, 1H), 4.98(s, 2H), 3.89(s, 3H), 3.79(s, 3H), 2.23(s, 3H) | 448(20), 205(62), 145(100), |
| 6 | CH | O | O | H | 3-CH$_3$—C$_6$H$_4$ | 7.62(s, 1H), 7.53~6.58(m, 12H), 5.62(d, 1H), 4.98(s, 2H), 3.78(s, 3H), 3.69(s, 3H), 2.29(s, 3H) | 448(29), 304(29), 205(72), 145(100) |
| 7 | CH | O | NH | H | 3-CH$_3$—C$_6$H$_4$ | 8.12(br, 1H), 7.72~6.54(m, 13H), 5.78(d, 1H), 4.98(s, 2H), 3.76(s, 6H), 2.85(d, 3), 2.34(s, 3H) | 447(9), 204(73), 144(100), |
| 8 | N | O | O | H | 3-CH$_3$—C$_6$H$_4$ | 7.72~6.52(m, 12H), 5.62(d, 1H), 4.98(s, 2H), 3.98(s, 3H), 3.78(s, 3H), 2.32(s, 3H) | 449(3), 145(40), 131(54), 161(100), 59(56) |
| 9 | CH | S | O | H | 3-CH$_4$—C$_6$H$_4$ | 7.85(s, 1H), 7.62~6.54(m, 12H), 5.59(d, 1H), 4.98(s, 2H), 3.67(s, 3H), 2.29(s, 3H), 2.27(s, 3H) | 464(8), 244(22), 221(51), 161(100), 115(35) |
| 10 | CH | O | O | H | 4-CH$_3$—C$_6$H$_4$ | 7.62(s, 1H), 7.53~6.58(m, 12H), 5.62(d, 1H), 4.98(s, 2H), 3.72(s, 3H), 3.69(s, 3H), 2.24(s, 3H) | 448(40), 304(30), 205(98), 145(100) |
| 11 | CH | O | NH | H | 4-CH$_3$—C$_6$H$_4$ | 8.12(br, 1H), 7.82~6.59(m, 13H), 5.62(d, 1H), 4.98(s, 2H), 3.69(s, 3H), 2.78(d, 3H), 2.28(s, 3H) | 447(20), 204(40), 144(100) |
| 12 | N | O | O | H | 4-CH$_3$—C$_6$H$_4$ | 7.78~6.58(m, 12H), 5.62(d, 1H), 4.92(s, 2H), 3.98(s, 3H), 3.79(s, 6H), 3.24(s, 3H) | 449(65), 260(85), 137(98), 116(100), 59(65) |
| 13 | CH | O | O | H | 3,4-(CH$_3$)$_2$—C$_6$H$_3$ | 7.62(s, 1H), 7.53~6.52(m, 11H), 5.63(d, 1H), 4.98(s, 2H), 3.78(s, 3H), 3.70(s, 3H), 2.27(s, 6H) | 462(46), 205(48), 145(100) |
| 14 | CH | O | NH | H | 3,4-(CH$_3$)$_2$—C$_6$H$_3$ | 8.12(br, 1H), 7.72~6.54(m, 12H), 5.78(d, 1H), 4.92(s, 2H), 3.62(s, 3H), 2.85(d, 3H), 2.21(s, 6H) | 461(9), 430(2), 204(70), 144(100) |
| 15 | N | O | O | H | 3,4-(CH$_3$)$_2$—C$_6$H$_3$ | 7.64~6.61(m, 11H), 5.71(d, 1H), 4.92(s, 2H), 3.92(s, 3H), 3.79(s, 3H), 2.28(s, 6H) | 463(40), 165(29), 137(91), 116(100), 59(69) |
| 16 | CH | S | O | H | 3,4-(CH$_3$)$_2$—C$_6$H$_3$ | 7.85(s, 1H), 7.62~6.52(m, 11H), 5.59(d, 1H), 4.98(s, 2H), 3.67(s, 3H), 2.29(s, 3H), 2.27(s, 6H) | 478(9), 258(4), 221(45), 161(100), 115(39) |
| 17 | CH | O | O | H | 3,5-(CH$_3$)$_2$—C$_6$H$_3$ | 7.62(s, 1H), 7.53~6.58(m, 11H), 5.62(d, 1H), 4.98(s, 2H), 3.78(s, 3H), 3.70(s, 3H), 2.28(s, 6H) | 462(51), 205(48), 145(100) |
| 18 | CH | O | NH | H | 3,5-(CH$_3$)$_2$—C$_6$H$_3$ | 8.12(br, 1H), 7.72~6.54(m, 12H), 5.78(d, 1H), 4.92(s, 2H), 3.62(s, 3H), 2.85(d, 3H), 2.21(s, 6H) | 461(6), 204(51), 144(100) |
| 19 | N | O | O | H | 3,5-(CH$_3$)$_2$—C$_6$H$_3$ | 7.64~6.61(m, 11H), 5.71(d, 1H), 4.92(s, 2H), 3.92(s, 3H), 3.79(s, 3H), 2.28(s, 6H) | 463(19), 206(23), 131(83), 116(100), 59(82) |
| 20 | CH | S | O | H | 3,5-(CH$_3$)$_2$—C$_6$H$_3$ | 7.85(s, 1H), 7.62~6.52(m, 11H), 5.59(d, 1H), 4.98(s, 2H), 3.67(s, 3H), 2.29(s, 3H), 2.27(s, 6H) | 478(9), 258(8), 221(52), 161(100), 115(37) |
| 21 | CH | O | O | H | 2,4,5-(CH$_3$)$_4$—C$_6$H$_2$ | 7.85(s, 1H), 7.84~6.59(m, 10H), 5.79(d, 1H), 4.92(s, 2H), 3.82(s, 3H), 3.78(s, 3H), 2.34(s, 9H) | 476(47), 205(77), 145(100), |
| 22 | CH | O | NH | H | 2,4,5-(CH$_3$)$_3$—C$_6$H$_2$ | 8.12(br, 1H), 7.72~6.54(m, 11H), 5.78(d, 1H), 4.92(s, 2H), 3.62(s, 3H), 2.85(d, 3H), 2.29(s, 9H) | 475(10), 272(7), 204(74), 144(100), 115(20) |
| 23 | N | O | O | H | 2,4,5-(CH$_3$)$_4$—C$_6$H$_2$ | 7.72~6.57(m, 10H), 5.68(d, 1H), 4.98(s, 2H), 3.89(s, 3H), 3.79(s, 6H), 2.28(s, 9H) | 477(31), 206(22), 131(72), 116(100), 59(60) |
| 24 | CH | S | O | H | 2,4,5-(CH$_3$)$_3$—C$_6$H$_2$ | 7.89(s, 1H), 7.72~6.52(m, 10H), 5.69(d, 1H), 4.92(s, 2H), 3.67(s, 3H), 2.42(s, 3H), 2.41~2.02(m, 9H) | 492(82), 272(4), 221(37), 161(100), 115(45) |
| 25 | CH | O | O | H | 3-CH$_4$O—C$_6$H$_4$ | 7.69(s, 1H), 7.62~6.54(m, 12H), 5.62(d, 1H), 4.98(s, 2H), 3.78(s, 3H), 3.72(s, 3H) | 464(32), 205(52), 145(100) |
| 26 | CH | O | NH | H | 3-CH$_4$O—C$_6$H$_4$ | 8.12(br, 1H), 7.72~6.54(m, 13H), 5.78(d, 1H), 4.98(s, 2H), 3.78(s, 6H), 3.75(s, 3H), 2.85(d, 3H) | 463(5), 260(5), 204(42), 144(100) |
| 27 | N | O | O | H | 3-CH$_4$O—C$_6$H$_4$ | 7.76~6.54(m, 12H), 5.68(d, 1H), 4.98(s, 2H), 3.97(s, 6H), 3.79(s, 3H), 3.68(d, 3H) | 465(41), 206(37), 131(57), 161(100), 59(56) |
| 28 | CH | S | O | H | 3-CH$_3$O—C$_6$H$_4$ | 7.85(s, 1H), 7.62~6.52(m, 12H), 5.59(d, 1H), 4.98(s, 2H), 3.67(s, 6H), 2.29(s, 3H) | 480(11), 260(10), 221(98), 161(100), 115(59) |

TABLE 3-continued

Compounds of formula (I)

| Compound No. | X | Y | Z | $R^1$ | $R^2$ | $^1$H—NMR (CDCl$_3$, TMS) δ (ppm) | MS (m/e) |
|---|---|---|---|---|---|---|---|
| 29 | CH | O | O | H | 4-CH$_3$O—C$_6$H$_4$ | 7.62(s, 1H), 7.53~6.58(m, 12H), 5.62(d, 1H), 4.98(s, 2H), 3.72(s, 6H), 3.69(s, 3H) | 464(35), 205(34), 145(100) |
| 30 | CH | O | NH | H | 4-CH$_3$O—C$_6$H$_4$ | 8.12(br, 1H), 7.82~6.59(m, 13H), 5.62(d, 1H), 4.98(s, 2H), 3.72(s, 3H), 3.69(s, 3H), 2.78(d, 3H) | 463(52), 260(40), 204(98), 144(100), 103(57) |
| 31 | N | O | O | H | 4-CH$_3$O—C$_6$H$_4$ | 7.72~6.62(m, 12H), 4.92(s, 2H), 3.91(s, 3H), 3.79(s, 6H) | 465(7), 384(22), 235(65), 207(63), 161(78), 43(100) |
| 32 | CH | O | O | H | 4-C$_6$H$_5$O—C$_6$H$_4$ | 7.68(s, 1H), 7.62~6.58(m, 17H), 5.68(d, 1H), 4.98(s, 2H), 3.89(s, 3H), 3.79(s, 3H) | 526(4), 205(98), 145(100) |
| 33 | N | O | O | H | 4-C$_6$H$_5$O—C$_6$H$_4$ | 7.72~6.54(m, 17H), 5.68(d, 1H), 4.98(s, 2H), 3.89(s, 3H), 3.79(s, 3H) | 527(42), 356(50), 263(26), 131(49), 116(100) |
| 34 | CH | O | O | H | 3-F—C$_6$H$_4$ | 7.54(s, 1H), 7.53~6.62(m, 12H), 5.62(d, 1H), 4.98(s, 2H), 3.68(s, 3H), 3.63(s, 3H) | 452(30), 205(89), 145(100), 103(52) |
| 35 | CH | O | NH | H | 3-F—C$_6$H$_4$ | 8.12(br, 1H), 7.68~6.64(m, 13H), 5.62(d, 1H), 4.98(s, 2H), 3.69(s, 3H), 2.78(d, 3H) | 451(40), 204(41), 144(100) |
| 36 | CH | O | O | H | 4-F—C$_6$H$_4$ | 7.57(s, 1H), 7.56~6.62(m, 12H), 5.62(d, 1H), 4.98(s, 2H), 3.79(s, 3H), 3.68(s, 3H) | 454(55), 205(99), 145(100), 103(44) |
| 37 | CH | O | O | H | 4-Cl—C$_6$H$_4$ | 7.62(s, 1H), 7.54~6.61(m, 12H), 5.62(d, 1H), 4.98(s, 2H), 3.72(s, 3H), 3.69(s, 3H) | 468(30), 205(35), 145(100) |
| 38 | CH | O | NH | H | 4-Cl—C$_6$H$_4$ | 8.12(br, 1H), 7.82~6.59(m, 13H), 5.62(d, 1H), 4.98(s, 2H), 3.69(s, 3H), 2.78(d, 3H) | 467(4), 204(45), 144(100) |
| 39 | N | O | O | H | 4-Cl—C$_6$H$_4$ | 7.71~6.52(m, 12H), 5.62(d, 1H), 4.92(s, 2H), 3.98(s, 3H), 3.72(s, 3H) | 469(19), 206(36), 131(54), 116(100) |
| 40 | CH | S | O | H | 4-Cl—C$_6$H$_4$ | 7.85(s, 1H), 7.62~6.54(m, 12H), 5.59(d, 1H), 4.98(s, 2H), 3.67(s, 3H), 2.39(s, 3H) | 484(3), 264(5), 221(60), 161(100), 115(41) |
| 41 | CH | O | O | H | C$_{10}$H$_7$ | 8.38~6.58(m, 16H), 6.39(d, 1H), 4.98(s, 2H), 3.72(s, 3H), 3.76(s, 3H) | 484(45), 205(83), 145(100) |
| 42 | CH | O | NH | H | C$_{10}$H$_7$ | 8.38~6.62(m, 17H), 6.51(d, 1H), 4.98(s, 2H), 3.72(s, 3H), 2.82(d, 3H) | 483(8), 204(55), 145(100), 103(27) |
| 43 | N | O | O | H | C$_{10}$H$_7$ | 8.28~6.52(m, 15H), 6.39(d, 1H), 4.98(s, 2H), 3.92(s, 3H), 3.76(s, 3H) | 485(27), 336(24)280(26), 170(41), 159(100), 116(91) |
| 44 | CH | S | O | H | C$_{10}$H$_7$ | 8.24~6.52(m, 16H), 6.25(d, 1H), 4.85(s, 2H), 3.67(s, 3H), 2.29(s, 3H) | 500(11), 280(7), 221(52), 161(100), 115(41) |

EXAMPLE 45

Preparation of methyl (2E)-3-methoxy-2-{2'-{3'-(2'''-fluoro-1'''-trifluoromethylstyryl)-2'''-oxy}phenoxymethyl}phenyl-2-propenoate (Compound 45)

The procedure of Example 1 was repeated except that 208 mg of the compound (1 mmol) obtained in the Preparation 22 was used in place of the compound obtained in Preparation 7 to obtain 462 mg (yield 92%) of the title compound as a colorless liquid.

$^1$H-NMR (CDCl$_3$, TMS) δ: 7.62(s, 1H), 7.58–6.52(m, 13H), 4.98(s, 2H), 3.72(s, 3H), 3.62(s, 3H); MS (m/e): 502(M$^+$, 7), 205(98), 145(100).

EXAMPLE 46

Preparation of (2E)-N-methyl-3-methoxy-2-{2'-{3"-(2'''-fluoro-1'''-trifluoromethylstyryl)-2'''-oxy}phenoxymethyl}phenyl-2-propenoamide (Compound 46)

The procedure of Example 2 was repeated except that 251 mg of the compound 45 (0.5 mmol) obtained in the Example 45 was used in place of the compound 1 obtained in Example 1 to obtain 213 mg (yield 85%) of the title compound as a colorless liquid.

$^1$H-NMR (CDCl$_3$, TMS) δ: 8.02(br, 1H), 7.72–6.53(m, 14H), 4.92(s, 2H), 3.69(s, 3H), 2.85(d, 3H); MS (m/e): 501(M$^+$, 13), 204(41), 145(100).

EXAMPLES 47 TO 107

Using each of the compounds obtained in Preparations 4 to 40, the procedure of Examples 1 or 2 was repeated to obtain 61 compounds (Compound 47 to 107) of formula (I) of the present invention having various R$^2$ groups, as shown in Table 4. The $^1$H-NMR and MS analysis data of these compounds are also listed in Table 4.

TABLE 4

Compounds of Formula (I)

| Compound No. | X | Y | Z | $R^1$ | $R^2$ | $^1$H—NMR (CDCl$_3$, TMS) δ (ppm) | MS (m/e) |
|---|---|---|---|---|---|---|---|
| 45 | CH | O | O | CF$_3$ | C$_6$H$_5$ | 7.62(s, 1H), 7.58–6.52(m, 13H), 4.98(s, 2H), 3.72(s, 3H), 3.62(s, 3H) | 502(7), 205(98), 145(100) |

TABLE 4-continued

Compounds of Formula (I)

| Compound No. | X | Y | Z | R¹ | R² | ¹H—NMR (CDCl₃, TMS) δ (ppm) | MS (m/e) |
|---|---|---|---|---|---|---|---|
| 46 | CH | O | NH | CF₃ | C₆H₅ | 8.02(br.s, 1H), 7.72–6.53(m, 14H), 4.92(s, 2H), 3.69(s, 3H), 2.85(d, 3H) | 501(13), 204(41), 144(100) |
| 47 | N | O | O | CF₃ | C₆H₅ | 7.52~6.52(m, 13H), 4.92(s, 2H), 3.92(s, 3H), 3.76(s, 3H) | 503(32), 472(30), 206(61), 131(75), 116(100), 59(96) |
| 48 | N | O | NH | CF₃ | C₆H₅ | 7.59–6.56(m, 14H), 4.91(s, 2H), 3.91(s, 3H), 2.89(d, 3H) | 502(3), 471(51), 414(96), 204(100), 116(98), 59(96) |
| 49 | CH | O | O | CF₃ | 3-CH₃—C₆H₄ | 7.62(s, 1H), 7.58–6.82(m, 12H), 4.98(s, 2H), 3.72(s, 3H), 3.62(s, 3H), 2.25(s, 3H) | 516(9), 205(97), 145(100) |
| 50 | CH | O | NH | CF₃ | 3-CH₃—C₆H₄ | 8.02(br.s, 1H), 7.72~6.53(m, 13H), 4.92(s, 2H), 3.69(s, 3H), 2.85(d, 3H), 2.45(s, 3H) | 515(29), 204(47), 1449100) |
| 51 | N | O | O | CF₃ | 3-CH₃—C₆H₄ | 7.57–6.52(m, 12H), 4.91(s, 2H), 3.96(s, 3H), 3.75(s, 3H), 2.29(s, 3H) | 517(3), 486(41), 206(94), 131(100), 116(92), 60(25) |
| 52 | N | O | NH | CF₃ | 3-CH₃—C₆H₄ | 7.49–6.51(m, 13H), 4.90(s, 2H), 3.82(s, 3H), 2.79(d, 3H), 2.29(s, 3H) | 516(7), 485(81), 428(97), 205(100), 174(99), 59(93) |
| 53 | CH | O | O | CF₃ | 4-CH₃—C₆H₄ | 7.67(s, 1H), 7.66–7.54(m, 12H), 4.96(s, 2H), 3.76(s, 3H), 3.69(s, 3H), 2.31(s, 3H) | 516(3), 485(10), 205(98), 145(100) |
| 54 | CH | O | NH | CF₃ | 4-CH₃—C₆H₄ | 8.02(br.s, 1H), 7.72–6.52(m, 13H), 4.92(s, 2H), 3.69(s, 3H), 2.83(d, 3H), 2.45(s, 3H) | 515(12), 204(72), 144(100) |
| 55 | N | O | O | CF₃ | 4-CH₃—C₆H₄ | 7.62–6.45(m, 12H), 4.93(s, 2H), 3.98(s, 3H), 3.84(s, 3H), 2.34(s, 3H) | 517(23), 206(28), 131(58), 116(100), 59(82) |
| 56 | N | O | NH | CF₃ | 4-CH₃—C₆H₄ | 7.52–6.55(m, 13H), 4.94(s, 2H), 3.87(s, 3H), 2.82(d, 3H), 2.30(s, 3H) | 516(3), 485(11), 205(100), 116(97), 59(94) |
| 57 | CH | S | O | CF₃ | 4-CH₃—C₆H₄ | 7.91(s, 1H), 7.69–6.52(m, 12H), 4.98(s, 2H), 3.72(s, 3H), 2.34(s, 3H), 2.31(s, 3H) | 532(8), 221(98), 161(100) 115(68) |
| 58 | CH | O | O | CF₃ | 4-C₂H₅—C₆H₄ | 7.62(s, 1H), 7.59–6.82(m, 12H), 4.98(s, 2H), 3.72(s, 3H), 3.62(s, 3H), 2.72(q, 2H), 1.29(t, 3H) | 530(8), 499(20), 205(89) 145(100) |
| 59 | CH | O | NH | CF₃ | 4-C₂H₅—C₆H₄ | 8.12(br.s, 1H), 7.72–6.52(m, 13H), 4.92(s, 2H), 3.69(s, 3H), 2.85(d, 3H), 2.78(q, 2H), 1.23(t, 3H) | 529(7), 204(98), 144(100), 115(23) |
| 60 | N | O | O | CF₃ | 4-C₂H₅—C₆H₄ | 7.56–6.52(m, 12H), 4.93(s, 3H), 3.97(s, 3H), 3.78(s, 3H), 2.65(q, 2H), 1.21(t, 3H) | 531(20), 500(15), 206(98), 131(100), 116(92), 60(56) |
| 61 | N | O | NH | CF₃ | 4-C₂H₅—C₆H₄ | 7.57–6.58(m, 13H), 4.95(s, 2H), 3.84(s, 3H), 2.83(d, 3H), 2.61(q, 2H), 1.23(t, 3H) | 530(15), 499(50), 442(87), 205(100), 116(98), 59(78) |
| 62 | CH | O | O | CF₃ | 4-n-C₄H₉—C₆H₄ | 7.61(s, 1H), 7.60–6.54(m, 12H), 4.96(s, 2H), 3.78(s, 3H), 3.64(s, 3H), 2.59(t, 2H), 1.70–1.24(m, 4H), 0.92(t, 3H) | 558(15), 205(96), 145(100), 131(80), 92(61) |
| 63 | CH | O | O | CF₃ | 3,4-(CH₃)₂—C₆H₃ | 7.63(s, 1H), 7.58–6.54(m, 11H), 4.96(s, 2H), 3.74(s, 3H), 3.61(s, 3H), 2.28(s, 3H), 2.21(s, 3H) | 530(12), 205(97), 145(100) |
| 64 | CH | O | NH | CF₃ | 3,4-(CH₃)₂—C₆H₄ | 8.02(br.s, 1H), 7.89–6.59(m, 12H), 4.92(s, 2H), 3.72(s, 3H), 2.82(d, 3H), 2.27(s, 3H), 2.21(s, 3H) | 529(9), 204(73), 144(100) |
| 65 | N | O | O | CF₃ | 3,4-(CH₃)₂—C₆H₄ | 7.64–6.61(m, 11H), 4.92(s, 2H), 3.92(s, 3H), 3.79(s, 3H), 2.28(s, 3H), 2.21(s, 3H) | 531(27), 500(17), 206(72), 116(100) |
| 66 | N | O | NH | CF₃ | 3,4-(CH₃)₂—C₆H₄ | 7.51–6.54(m, 12H), 4.91(s, 2H), 3.89(s, 3H), 2.82(d, 3H), 2.28(s, 3H), 2.23(s, 3H) | 530(30), 499(12), 205(100) 174(43), 116(98), 59(93) |
| 67 | CH | O | O | CF₃ | 3,5-(CH₃)₂—C₆H₃ | 7.62(s, 1H), 7.58–6.52(m, 11H), 4.98(s, 2H), 3.72(s, 3H), 3.62(s, 3H), 2.31(s, 3H), 2.26(s, 3H) | 530(24), 499(6), 205(96) 145(100) |
| 68 | CH | O | NH | CF₃ | 3.5-(CH₃)₂—C₆H₃ | 8.02(br.s, 1H), 7.72–6.51(m, 12H), 4.92(s, 2H), 3.72(s, 3H), 2.85(d, 3H), 2.30(s, 3H), 2.25(s, 3H) | 529(7), 204(53), 144(100) |
| 69 | N | O | O | CF₃ | 3,5-(CH₃)₂—C₆H₄ | 7.52–6.52(m, 11H), 4.92(d, 2H), 3.92(s, 3H), 3.76(s, 3H), 2.30(s, 3H), 2.25(s, 3H) | 53(3), 500(10), 206(61), 131(37), 116(100) |
| 70 | N | O | NH | CF₃ | 3,5-(CH₃)₂—C₆H₄ | 7.49–6.57(m, 12H), 4.92(s, 2H), 3.87(s, 3H), 2.83(d, 3H), 2.32(s, 3H), 2.26(s, 3H) | 530(24), 442(59), 205(100), 174(98), 116(92) |
| 71 | CH | O | O | CF₃ | 3-CH₃O—C₆H₄ | 7.62(s, 1H), 7.58–6.82(m, 12H), 4.98(s, 2H), 3.81(s, 3H), 3.71(s, 3H), 3.62(s, 3H) | 532(70), 468(60), 205(98), 145(100) |
| 72 | CH | O | NH | CF₃ | 3-CH₃O—C₆H₄ | 8.02(br.s, 1H), 7.72–6.52(m, 13H), 4.92(s, 2H), 3.72(s, 3H), 3.67(s, 3H), 2.85(d, 3H) | 531(25), 422(82), 204(87), 144(100), 115(43) |
| 73 | N | O | O | CF₃ | 3-CH₃O—C₆H₄ | 7.62 . 6.45(m, 12H), 4.93(s, 2H), 3.98(s, 3H), 3.84(s, 3H), 3.73(s, 3H) | 533(8), 502(50), 206(45), 131(40), 161(100) |
| 74 | N | O | NH | CF₃ | 3-CH₃O—C₆H₄ | 7.51–6.52(m, 13H), 4.91(s, 2H), 3.87(s, 3H), 3.72(s, 3H), 2.82(d, 3H) | 532(20), 205(100), 174(58), 116(98), 59(87) |
| 75 | CH | O | NH | CF₃ | 4-CH₃O—C₆H₄ | 8.02(br.s, 1H), 7.69–6.54(m, 13H), 4.93(s, 2H), 3.74(s, 3H), 3.60(s, 3H), 2.89(d, 3H) | 531(31), 204(98), 144(100) |
| 76 | N | O | O | CF₃ | 4-CH₃O—C₆H₄ | 7.72–6.62(m, 12H), 4.93(s, 2H), 3.91(s, 3H), 3.82(s, 3H), 3.74(s, 3H) | 533(7), 384(22), 235(65), |
| 77 | N | O | NH | CF₃ | 4-CH₃O—C₆H₄ | 7.51–6.59(m, 13H), 4.94(s, 2H), 3.89(s, 3H), 3.76(s, 3H), 2.85(d, 3H) | 532(15), 444(76), 205(97), 174(100), 116(82) |
| 78 | CH | O | O | CF₃ | 4-C₂H₅O—C₆H₄ | 7.60(s, 1H), 7.57–6.55(m, 12H), 4.94(s, 2H), 4.01(q, 2H), 3.78(s, 3H), 3.69(s, 3H), 1.40(t, 3H) | 546(3), 205(94), 145(100) |
| 79 | N | O | O | CF₃ | 4-C₂H₅O—C₆H₄ | 7.56–6.50(m, 12H), 4.91(s, 2H), 3.98(q, 2H), 3.49(s, 3H), 3.79(s, 3H), 1.38(t, 3H) | 547(14), 516(30), 206(49), 131(95), 116(100) |
| 80 | N | O | NH | CF₃ | 4-C₂H₅O—C₆H₄ | 7.48–6.55(m, 13H), 4.91(s, 2H), 3.99(q, 2H), 2.86(s, 3H), 2.82(d, 3H), 1.36(t, 3H) | 546(40), 458(56), 205(100), 174(94), 116(96) |
| 81 | CH | O | O | CF₃ | 3,4-OCH₂O—C₆H₃ | 7.61(s, 1H), 7.60–6.57(m, 11H), 5.91(s, 2H), 4.97(s, 2H), 3.79(s, 3H), 3.68(s, 3H) | 546(4), 205(65), 145(100) |
| 82 | N | O | O | CF₃ | 3,4-OCH₂O—C₆H₃ | 7.55–6.51(m, 11H), 5.94(s, 2H), 4.92(s, 2H), 3.99(s, 3H), 3.81(s, 3H) | 547(8), 516(15), 131(57), 116(100), 60(49) |

TABLE 4-continued

Compounds of Formula (I)

| Compound No. | X | Y | Z | R¹ | R² | ¹H—NMR (CDCl₃, TMS) δ (ppm) | MS (m/e) |
|---|---|---|---|---|---|---|---|
| 83 | CH | O | O | CF₃ | 3-CF₃—C₆H₄ | 7.82–6.56(m, 13H), 4.95(s, 2H), 3.78(s, 3H), 3.68(s, 3H) | 570(4), 219(72), 205(60), 145(100) |
| 84 | CH | O | O | CF₃ | 3-Cl—C₆H₄ | 7.62(s, 1H), 7.58–6.52(m, 12H), 4.92(s, 2H), 3.72(s, 3H), 3.62(s, 3H) | 536(7), 205(51), 145(100) |
| 85 | CH | O | NH | CF₃ | 3-Cl—C₆H₄ | 8.01(br.s, 1H), 7.70–6.49(m, 13H), 4.95(s, 2H), 3.59(s, 3H), 2.89(d, 3H) | 535(27), 204(99), 144(100) |
| 86 | N | O | O | CF₃ | 3-Cl—C₆H₄ | 7.68–6.52(m, 12H), 4.92(s, 2H), 3.89(s, 3H), 3.76(s, 3H) | 537(8), 206(39), 131(98), 116(100) |
| 86 | N | O | NH | CF₃ | 3-Cl—C₆H₄ | 7.53–6.58(m, 13H), 4.94(s, 2H), 3.89(s, 3H), 2.85(d, 3H) | 536(23), 448(56), 205(97), 174(79), 117(100) |
| 88 | CH | O | O | CF₃ | 4-Cl—C₆H₄ | 7.63(s, 1H), 7.58–6.82(m, 12H), 4.98(s, 2H), 3.78(s, 3H), 3.68(s, 3H) | 536(7), 205(48), 145(100) |
| 89 | CH | O | NH | CF₃ | 4-Cl—C₆H₄ | 8.02(br.s, 1H), 7.72–6.53(m, 13H), 4.93(s, 2H), 3.69(s, 3H), 2.83(d, 3H) | 535(6), 204(78), 144(100) |
| 90 | N | O | O | CF₃ | 4-Cl—C₆H₄ | 7.82–7.45(m, 12H), 4.98(s, 2H), 3.97(s, 3H), 3.79(s, 3H) | 537(9), 506(13), 206(89), 131(98), 116(100), 59(68) |
| 91 | N | O | NH | CF₃ | 4-Cl—C₆H₄ | 7.51–6.52(m, 13H), 4.92(s, 2H), 3.84(s, 3H), 2.82(d, 3H) | 536(25), 506(13), 205(97), 174(89), 116(100), 59(69) |
| 92 | CH | O | O | CF₃ | 3-F—C₆H₄ | 7.62(s, 1H), 7.58–6.62(m, 12H), 4.98(s, 2H), 3.72(s, 3H), 3.62(s, 3H) | 520(12), 205(98), 145(100) |
| 93 | CH | O | NH | CF₃ | 3-F—C₆H₄ | 8.12(br.s, 1H), 7.72–6.53(m, 13H), 4.93(s, 2H), 3.67(s, 3H), 2.84(d, 3H) | 519(25), 204(98), 172(31), 144(100), 115(46) |
| 94 | N | O | O | CF₃ | 3-F—C₆H₄ | 7.54–6.51(m, 12H), 4.92(s, 2H), 3.98(s, 3H), 3.78(s, 3H) | 521(15), 490(56), 206(98), 146(75), 132(89), 116(100) |
| 95 | N | O | NH | CF₃ | 3-F—C₆H₄ | 7.44–6.55(m, 13H), 4.90(s, 2H), 3.85(s, 3H), 2.80(d, 3H) | 520(25), 432(48), 205(100), 174(82), 116(98) |
| 96 | CH | O | O | CF₃ | 4-F—C₆H₄ | 7.64(s, 1H), 7.58–6.52(m, 12H), 4.97(s, 2H), 3.74(s, 3H), 3.64(s, 3H) | 520(8), 205(28), 145(98), 84(100) |
| 97 | CH | O | NH | CF₃ | 4-F—C₆H₄ | 8.12(br.s, 1H), 7.71–6.43(m, 13H), 4.93(s, 2H), 3.60(s, 3H), 2.89(d, 3H) | 519(21), 204(99), 144(100) |
| 98 | N | O | O | CF₃ | 4-F—C₆H₄ | 7.56–6.53(m, 12H), 4.94(s, 2H), 3.99(s, 3H), 3.80(s, 3H) | 521(5), 490(40), 206(92), 131(100), 116(98), 60(49) |
| 99 | N | O | NH | CF₃ | 4-F—C₆H₄ | 7.52–6.53(m, 13H), 4.94(s, 2H), 3.87(s, 3H), 2.82(d, 3H) | 520(16), 489(75), 207(51), 116(100), 59(87) |
| 100 | CH | O | O | CF₃ | 4-Br—C₆H₄ | 7.69(s, 1H), 7.61–6.53(m, 12H), 4.96(s, 2H), 3.76(s, 3H), 3.68(s, 3H) | 580(4), 205(92), 145(100) |
| 101 | CH | O | NH | CF₃ | 4-Br—C₆H₄ | 8.09(br.s, 1H), 7.59–6.50(m, 13H), 4.96(s, 2H), 3.62(s, 3H), 2.92(d, 3H) | 579(4), 204(97), 144(100) |
| 102 | CH | O | O | CF₃ | 3,5-Cl₂—C₆H₄ | 7.61(s, 1H), 7.60–6.56(m, 11H), 4.96(s, 2H), 3.80(s, 3H), 3.68(s, 3H) | 570(6), 205(98), 145(100) |
| 103 | N | O | O | CF₃ | 3,5-Cl₂—C₆H₃ | 7.57–6.56(m, 11H), 4.96(s, 2H), 4.00(s, 3H), 3.82(s, 3H) | 571(16), 540(38), 206(57), 131(100), 116(98), 60(81) |
| 104 | N | O | NH | CF₃ | 3,5-Cl₂—C₆H₃ | 7.47–6.55(m, 12H), 4.92(s, 2H), 3.87(s, 3H), 2.82(d, 3H) | 570(23), 482(30), 205(100), 174(92), 116(82) |
| 105 | CH | O | O | CF₃ | C₄H₃S-2-yl | 7.68(s, 1H), 7.63–6.43(m, 11H), 4.95(s, 2H), 3.74(s, 3H), 3.63(s, 3H) | 508(5), 205(70), 145(100) |
| 106 | CH | O | O | CF₃ | n-C₆H₁₃ | 7.68(s, 1H), 7.61–6.58(m, 8H), 4.95(s, 2H), 3.81(s, 3H), 3.69(s, 3H), 2.19(t, 2H), 1.62–1.18(m, 8H), 0.89(t, 3H) | 510(3), 205(64), 145(100) |
| 107 | CH | O | NH | CF₃ | n-C₆H₁₃ | 8.10(br.s, 1H), 7.67–6.61(m, 9H), 4.99(s, 2H), 3.68(s, 3H), 2.97(d, 3H), 2.21(t, 2H), 1.61–1.21(m, 8H)m 0.91(t, 3H) | 509(10), 204(99), 144(100) |

Fungicidal Activity Test

To examine fungicidal activity of the compounds of the present invention, each of the compounds listed in Table 3 and 4 was dissolved in 10% acetone to a concentration of 250 ppm, and Tween-20 was added thereto to a concentration of 250 or 500 ppm. 50 ml of the resulting solution was sprayed on leaves of a host plant. The plant was kept at room temperature for 24 hours to let the solvent evaporate, and then, a pathogenic fungus was inoculated thereonto. The plant was held in a humidity chamber for 24 hours, transferred to an plant growth room kept at 20 to 27° C. and a relative humidity of 60 to 80% and kept to induce disease. Subsequently, the lesion area(L.A.) attacked by the pathogenic fungus was measured according to a method of Cho(Cho, K. Y., Search Report by Korea Research Institute of Chemical Technology (1989))". This procedure was repeated twice for each test. 10% Acetone solution containing 250 ppm of Tween-20 was used as a control.

The fungicidal activity of the compound of the present invention is repressed by a control value (C.V.) calculated as;

$$C.V. \ (\%) = \frac{L.A. \ of \ control - L.A. \ of \ test}{L.A. \ of \ control} \times 100$$

TEST EXAMPLE 1

Fungicidal Activity Against Rice Blast (RCB) Disease

*Pyricularia oryzae* Carvara KA301 was inoculated on a rice bran agar medium (rice bran 20 g, dextrose 10 g, agar 15 g and distilled water 1 l) and cultured at 26° C. for 1 week. The surface of the medium was scratched using a rubber polishman to remove aerial mycelia, and cultured under a fluorescent light for 48 hours to form a spore. Spores were suspended in sterilized water at a concentration of $1\times10^6$ spore/ml. The spore suspension was sprayed enough to soak the leaves of a RBC disease-sensitive Nakdong rice plant having 3 or 4 leaves. The rice plant was held in a humidified dark room for 24 hours, transferred to an incubator kept at 24 to 28° C. and a relative humidity of more than 80% and kept for 5 days to induce RCB. L.A. on a fully grown leaf appearing underneath an uppermost leaf was measured to calculate an C.V.

TEST EXAMPLE 2

Fungicidal Activity Against Rice Sheath Blight (RSB) Disease

*Rhizoctonia solani* AG-1 was cultured on a PDA medium (potato 200 g, dextrose 20 g, agar 20 g and distilled water 1 l) for 3 days and the agar disc (diameter 0.6 cm) was inoculated and cultured on sterilized wheat bran medium in a 1 l bottle at 26 to 28° C. for 7 days. A mycelial mass was ground using a homogenizer, inoculated uniformly on soil of a pot wherein a Nakdong rice plant having 2 or 3 leaves and an height of 5 cm grew, and kept in humidity polyvinyl chamber for 5 days to induce RSB. L.A. on a leaf sheath was measured to calculate an C.V.

TEST EXAMPLE 3

Fungicidal Activity Against Cucumber Gray Mold Rot (CGM) Disease

*Botrytis cinerae*, which was isolated from cucumber infected thereby, was inoculated on a PDA agar medium and cultured under a 12L/12D cycle at 25° C. for 15 days to form spore. The spores were scraped, filtered through a gauze and then suspended in potato dextrose liquid medium at a concentration of $1\times10^6$ spore/ml. The spore suspension was sprayed on a cucumber plant having one leaf. The cucumber plant was held in a humidified room at 20° C. for 3 days. L.A. on a leaf was measured to calculate an C.V.

TEST EXAMPLE 4

Fungicidal Activity on Tomato Late Blight (TLB) Disease

*Phytophthora infestans* was cultured on a juice agar medium (V-8 juice 200 ml, $CaCO_3$ 4.5 g, agar 15 g and distilled water 800 ml) under a 16L/8D cycle at 20° C. for 14 days. Sterilized water was added thereto, the vessel was shaken to free zoospore sacs from the fungus mass and the zoospore sacs were collected using a four-layered gauze. A zoospore sac suspension having a concentration of $1\times10^5$ spore/ml was sprayed on a young tomato plant. The tomato plant was held in a humidified room at 20° C. for 24 hours, transferred to an incubator maintained at a temperature of 20° C. and a relative humidity of more than 80% for 4 days and cultured in to induce RBC. L.A. on primary and secondary leaves was measured to calculate an C.V.

TEST EXAMPLE 5

Fungicidal Activity Against Wheat Leaf Rust (WLR) Disease

*Puccinia recondita* was subcultured on a wheat plant in a laboratory. 15 g of wheat seeds was sowed in a pot (diameter 6.5 cm) and cultured in a greenhouse for 7 days to obtain a wheat plant having only a primary leaf. The wheat plant was inoculated with spores by shaking thereover another plant infected thereby. The inoculated wheat plant was held in a humidified room at 20° C. for 24 hours, transferred to an incubator maintained at a temperature of 20° C. and a relative humidity of 70% and cultured for 10 days to induce WLR. L.A. on the primary leaf was measured to calculate an C.V.

TEST EXAMPLE 6

Fungicidal Activity Against Barley Powdery Mildew (BPM) Disease

*Erysiphae graminis* was subcultured on a wheat plant in a laboratory. 15 g of barley seeds was sowed in a pot (diameter 6.5 cm) and cultured in a greenhouse for 7 days to obtain a barley plant having only a primary leaf. The barley plant was inoculated with spores by shaking thereover another plant infected by BPM. The inoculated barley plant was cultured in an incubator maintained at a temperature of 22 to 24° C. and a relative humidity of 50% for 7 days to induce BPM. L.A. on the leaf was measured to calculate an C.V.

The results of subjecting the compounds of the present invention in Test example 1 to 6 at a concentration level of 250 ppm was more than 90% in most cases.

Accordingly, these compounds having a C.V. of more than 90% were subjected to another series of tests at a reduced concentration level of 50 ppm and the results are shown in Table 5.

TABLE 5

| Compound No. | Fungicidal Activities at 50 ppm C. V. (%) | | | | | |
|---|---|---|---|---|---|---|
| | RCB | RSB | CGM | TLB | WLR | BPM |
| 1 | 97 | 95 | 62 | 70 | 100 | 100 |
| 2 | 100 | 50 | 84 | 74 | 96 | 86 |
| 3 | 100 | 70 | 15 | 70 | 93 | 41 |
| 4 | 90 | 75 | 33 | 86 | 85 | 91 |
| 5 | 95 | 95 | 0 | 50 | 100 | 99 |
| 6 | 100 | 65 | 41 | 86 | 98 | 100 |
| 7 | 26 | 10 | 33 | 46 | 0 | 0 |
| 8 | 100 | 92 | 51 | 92 | 98 | 97 |
| 9 | 96 | 92 | 33 | 26 | 88 | 95 |
| 10 | 97 | 92 | 0 | 50 | 100 | 95 |
| 11 | 16 | 5 | 15 | 20 | 43 | 25 |
| 12 | 100 | 80 | 27 | 84 | 93 | 94 |
| 13 | 97 | 50 | 58 | 85 | 98 | 100 |
| 14 | 16 | 5 | 63 | 20 | 16 | 25 |
| 15 | 92 | 90 | 15 | 25 | 96 | 100 |
| 16 | 53 | 60 | 0 | 33 | 83 | 97 |
| 17 | 90 | 60 | 50 | 81 | 100 | 99 |
| 18 | 26 | 5 | 21 | 6 | 0 | 0 |
| 19 | 100 | 90 | 0 | 33 | 100 | 98 |
| 20 | 73 | 35 | 0 | 46 | 83 | 93 |
| 21 | 93 | 90 | 33 | 44 | 96 | 98 |
| 22 | 0 | 26 | 0 | 25 | 0 | 0 |
| 23 | 88 | 90 | 20 | 10 | 93 | 100 |
| 24 | 62 | 46 | 27 | 18 | 98 | 96 |
| 25 | 95 | 92 | 0 | 43 | 100 | 98 |
| 26 | 20 | 35 | 0 | 55 | 70 | 88 |
| 27 | 100 | 90 | 0 | 80 | 86 | 96 |
| 28 | 93 | 70 | 21 | 73 | 91 | 97 |
| 29 | 93 | 90 | 28 | 56 | 100 | 99 |
| 30 | 93 | 5 | 28 | 6 | 0 | 16 |
| 31 | 93 | 30 | 0 | 84 | 93 | 50 |
| 32 | 30 | 30 | 20 | 24 | 88 | 90 |
| 33 | 20 | 5 | 20 | 10 | 83 | 94 |
| 34 | 99 | 95 | 0 | 75 | 98 | 100 |
| 35 | 15 | 30 | 35 | 35 | 40 | 58 |
| 36 | 100 | 95 | 0 | 66 | 100 | 99 |
| 37 | 95 | 45 | 58 | 93 | 98 | 98 |

TABLE 5-continued

Fungicidal Activities at 50 ppm

| Compound No. | RCB | RSB | CGM | TLB | WLR | BPM |
|---|---|---|---|---|---|---|
| 38 | 33 | 5 | 15 | 33 | 0 | 8 |
| 39 | 100 | 90 | 15 | 80 | 86 | 96 |
| 40 | 73 | 70 | 9 | 33 | 83 | 93 |
| 41 | 86 | 65 | 46 | 31 | 93 | 99 |
| 42 | 37 | 26 | 0 | 33 | 73 | 16 |
| 43 | 90 | 73 | 21 | 40 | 97 | 98 |
| 44 | 93 | 10 | 0 | 46 | 66 | 93 |
| 45 | 90 | 94 | 0 | 0 | 100 | 100 |
| 46 | 0 | 20 | 27 | 11 | 53 | 0 |
| 47 | 96 | 90 | 26 | 64 | 86 | 98 |
| 48 | 97 | 45 | 28 | 70 | 100 | 98 |
| 49 | 95 | 50 | 41 | 0 | 100 | 100 |
| 50 | 0 | 25 | 5 | 33 | 0 | 0 |
| 51 | 41 | 60 | 0 | 3 | 100 | 100 |
| 52 | 95 | 90 | 28 | 55 | 100 | 100 |
| 53 | 100 | 50 | 55 | 0 | 100 | 100 |
| 54 | 16 | 20 | 9 | 20 | 16 | 41 |
| 55 | 100 | 30 | 0 | 85 | 100 | 100 |
| 56 | 97 | 65 | 0 | 48 | 100 | 100 |
| 57 | 53 | 45 | 9 | 40 | 96 | 98 |
| 58 | 90 | 40 | 25 | 0 | 100 | 100 |
| 59 | 12 | 33 | 0 | 33 | 0 | 0 |
| 60 | 0 | 40 | 0 | 18 | 98 | 100 |
| 61 | 100 | 50 | 5 | 64 | 100 | 100 |
| 62 | 0 | 35 | 28 | 3 | 93 | 98 |
| 63 | 75 | 40 | 25 | 25 | 100 | 100 |
| 64 | 16 | 0 | 0 | 22 | 0 | 0 |
| 65 | 91 | 90 | 16 | 33 | 99 | 99 |
| 66 | 98 | 40 | 0 | 18 | 100 | 100 |
| 67 | 80 | 50 | 16 | 25 | 100 | 100 |
| 68 | 0 | 0 | 0 | 22 | 56 | 0 |
| 69 | 58 | 75 | 38 | 33 | 100 | 100 |
| 70 | 100 | 0 | 0 | 0 | 100 | 100 |
| 71 | 90 | 40 | 41 | 62 | 100 | 100 |
| 72 | 0 | 33 | 0 | 33 | 0 | 0 |
| 73 | 93 | 92 | 9 | 60 | 98 | 93 |
| 74 | 100 | 70 | 52 | 64 | 100 | 100 |
| 75 | 0 | 40 | 0 | 33 | 0 | 0 |
| 76 | 63 | 90 | 0 | 44 | 96 | 99 |
| 77 | 99 | 60 | 11 | 82 | 100 | 100 |
| 78 | 0 | 40 | 0 | 0 | 98 | 100 |
| 79 | 0 | 55 | 7 | 18 | 100 | 100 |
| 80 | 100 | 0 | 0 | 0 | 100 | 100 |
| 81 | 86 | 65 | 0 | 33 | 100 | 100 |
| 82 | 50 | 45 | 0 | 0 | 98 | 100 |
| 83 | 25 | 50 | 0 | 11 | 100 | 100 |
| 84 | 90 | 25 | 16 | 81 | 100 | 100 |
| 85 | 16 | 10 | 16 | 22 | 73 | 0 |
| 86 | 90 | 90 | 27 | 22 | 100 | 100 |
| 87 | 100 | 0 | 0 | 0 | 100 | 100 |
| 88 | 92 | 25 | 25 | 31 | 98 | 100 |
| 89 | 0 | 25 | 22 | 33 | 33 | 0 |
| 90 | 90 | 30 | 25 | 0 | 100 | 99 |
| 91 | 99 | 90 | 17 | 64 | 100 | 100 |
| 92 | 93 | 55 | 16 | 81 | 100 | 100 |
| 93 | 0 | 5 | 0 | 0 | 73 | 0 |
| 94 | 41 | 60 | 0 | 40 | 100 | 100 |
| 95 | 100 | 72 | 0 | 0 | 100 | 100 |
| 96 | 90 | 67 | 33 | 62 | 100 | 100 |
| 97 | 0 | 10 | 11 | 22 | 83 | 33 |
| 98 | 33 | 65 | 0 | 25 | 100 | 100 |
| 99 | 80 | 90 | 21 | 48 | 100 | 100 |
| 100 | 16 | 45 | 0 | 0 | 100 | 100 |
| 101 | 0 | 10 | 21 | 3 | 73 | 0 |
| 102 | 0 | 45 | 0 | 3 | 96 | 100 |
| 103 | 0 | 60 | 0 | 3 | 100 | 100 |
| 104 | 100 | 50 | 0 | 0 | 100 | 100 |
| 105 | 96 | 78 | 0 | 0 | 100 | 70 |
| 106 | 0 | 45 | 0 | 0 | 98 | 100 |
| 107 | 0 | 10 | 21 | 3 | 80 | 41 |

As can be seen from Table 5, the compounds of the present invention have a broad fungicidal activity spectrum against RCB, RSB, WLR and BPM.

Those compounds having a C.V. of more than 90% at 50 ppm level were subjected to Test Example 1, 2, 5 and 6 again at a 10 ppm concentration level and the results are shown in Table 6, 7, 8 and 9, respectively.

TABLE 6

Fungicidal Activities against RCB at 10 ppm

| Compound No. | C. V. (%) |
|---|---|
| 5 | 94 |
| 6 | 96 |
| 8 | 90 |
| 10 | 95 |
| 13 | 97 |
| 17 | 95 |
| 25 | 95 |
| 29 | 92 |
| 34 | 100 |
| 36 | 94 |
| 37 | 100 |
| 45 | 90 |
| 48 | 100 |
| 52 | 95 |
| 55 | 94 |
| 56 | 92 |
| 61 | 96 |
| 66 | 100 |
| 70 | 100 |
| 74 | 93 |
| 77 | 96 |
| 80 | 95 |
| 84 | 95 |
| 87 | 100 |
| 90 | 93 |
| 91 | 99 |
| 95 | 100 |
| 96 | 95 |
| 99 | 95 |
| 104 | 98 |

TABLE 7

Fungicidal Activities against RSB at 10 ppm

| Compound No. | C. V. (%) |
|---|---|
| 45 | 94 |
| 48 | 90 |

TABLE 8

Fungicidal Activities against WLB at 10 ppm

| Compound No. | C. V. (%) |
|---|---|
| 1 | 96 |
| 5 | 95 |
| 6 | 91 |
| 8 | 90 |
| 10 | 96 |
| 12 | 97 |
| 13 | 95 |
| 17 | 99 |
| 21 | 90 |
| 23 | 91 |
| 25 | 99 |
| 29 | 99 |

TABLE 8-continued

Fungicidal Activities against WLB at 10 ppm

| Compound No. | C. V. (%) |
|---|---|
| 34 | 100 |
| 36 | 100 |
| 37 | 97 |
| 41 | 95 |
| 45 | 100 |
| 48 | 100 |
| 49 | 95 |
| 51 | 90 |
| 52 | 100 |
| 53 | 99 |
| 56 | 100 |
| 58 | 95 |
| 60 | 93 |
| 61 | 100 |
| 65 | 100 |
| 66 | 100 |
| 69 | 95 |
| 70 | 100 |
| 71 | 95 |
| 73 | 96 |
| 74 | 100 |
| 76 | 99 |
| 77 | 100 |
| 78 | 97 |
| 79 | 96 |
| 80 | 100 |
| 81 | 100 |
| 82 | 96 |
| 83 | 94 |
| 84 | 97 |
| 86 | 96 |
| 87 | 100 |
| 88 | 93 |
| 91 | 100 |
| 92 | 100 |
| 94 | 95 |
| 95 | 100 |
| 96 | 97 |
| 98 | 96 |
| 99 | 100 |
| 100 | 95 |
| 103 | 96 |
| 104 | 100 |
| 105 | 96 |
| 106 | 91 |

TABLE 9

Fungicidal activities against TLB at 10 ppm

| Compound No. | C. V. (%) |
|---|---|
| 1 | 100 |
| 5 | 94 |
| 6 | 100 |
| 8 | 93 |
| 10 | 97 |
| 12 | 96 |
| 13 | 99 |
| 23 | 91 |
| 25 | 91 |
| 27 | 97 |
| 29 | 90 |
| 34 | 100 |
| 36 | 100 |
| 37 | 100 |
| 39 | 95 |
| 45 | 100 |
| 47 | 98 |
| 48 | 100 |
| 49 | 100 |
| 51 | 98 |
| 52 | 100 |
| 53 | 96 |
| 55 | 97 |
| 56 | 100 |
| 58 | 99 |
| 60 | 97 |
| 61 | 100 |
| 63 | 100 |
| 65 | 94 |
| 66 | 100 |
| 67 | 100 |
| 69 | 95 |
| 70 | 100 |
| 71 | 100 |
| 73 | 88 |
| 74 | 100 |
| 76 | 96 |
| 77 | 100 |
| 78 | 100 |
| 79 | 99 |
| 80 | 100 |
| 81 | 100 |
| 82 | 97 |
| 83 | 100 |
| 84 | 100 |
| 86 | 95 |
| 87 | 100 |
| 88 | 100 |
| 90 | 97 |
| 91 | 100 |
| 92 | 99 |
| 94 | 99 |
| 95 | 100 |
| 96 | 100 |
| 98 | 98 |
| 99 | 100 |
| 100 | 99 |
| 102 | 98 |
| 103 | 100 |
| 104 | 100 |
| 106 | 100 |

As can be seen from Tables 6 to 9, the compounds of the present invention are very active in controlling fungicidal plant disease even at a 10 ppm.

While the invention has been described with respect to the specific embodiments, it should be recognized that various modifications and changes may be made by those skilled in the art to the invention which also fall within the scope of the invention as defined by the appended claims.

What is claimed is:

1. A compound of formula (I) or a stereoisomer thereof:

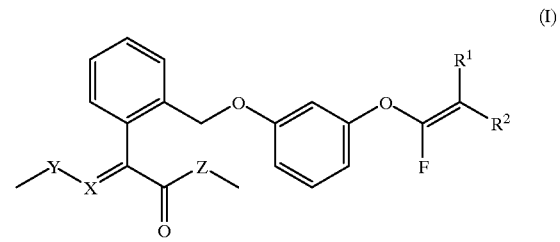

(I)

wherein:
X is CH or N;
Y is O or S;

Z is O or NH;

R¹ is hydrogen or CF₃; and

R² is hydrogen, a $C_{1-10}$ alkyl, naphthyl, thiophenyl or phenyl group optionally carrying one or more substituents selected from the group consisting of $C_{1-6}$ alkyl, halogen-substituted $C_{1-6}$ alkyl, $C_{1-6}$ alkoxy, phenoxy, halogen, and methylenedioxy radicals.

2. The compound of claim 1 wherein Y is O; Z is O; R¹ is hydrogen; and R² is a naphthyl or phenyl group optionally substituted with a methyl, methoxy or halogen radical.

3. The compound of claim 1 wherein Y is O; R¹ is CF₃; and R² is a phenyl group optionally substituted with methyl, methoxy or halogen radical.

4. A process for the preparation of the compound of claim 1 which comprises (a) reacting a compound of formula (II) with 3-hydroxyphenol in the presence of a base to obtain a compound of formula (III); and (b) reacting the compound of formula (III) with a compound formula (IV) in the presence of a base:

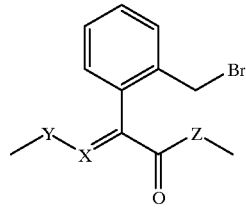
(II)

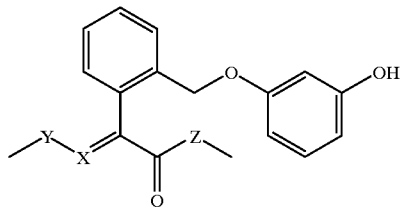
(III)

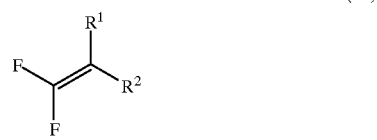
(IV)

wherein, X, Y, Z, R¹ and R² have the same meanings as defined in claim 1.

5. An fungicidal composition comprising a fungicidally effective amount of the compound of claim 1 as an active ingredient and an inert carrier.

* * * * *